(12) United States Patent
Miyazaki et al.

(10) Patent No.: US 7,317,189 B2
(45) Date of Patent: Jan. 8, 2008

(54) X-RAY CT APPARATUS, RADIATION DETECTOR AND METHOD FOR READING OUT ELECTRIC SIGNALS OF A RADIATION DETECTOR

(75) Inventors: Hiroaki Miyazaki, Otawara (JP); Hiroshi Aradate, Otawara (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 129 days.

(21) Appl. No.: 11/120,987

(22) Filed: May 4, 2005

(65) Prior Publication Data
US 2005/0253078 A1 Nov. 17, 2005

(30) Foreign Application Priority Data
May 11, 2004 (JP) ............................ 2004-141163

(51) Int. Cl.
*G01T 1/24* (2006.01)
(52) U.S. Cl. .................... 250/370.09; 378/19
(58) Field of Classification Search ............ 250/370.09
See application file for complete search history.

(56) References Cited

U.S. PATENT DOCUMENTS

| 4,220,863 | A | * | 9/1980 | McBride et al. | .............. | 378/10 |
| 5,986,278 | A | * | 11/1999 | Becker et al. | .............. | 250/580 |
| 6,396,898 | B1 | | 5/2002 | Saito et al. | | |
| 6,760,404 | B2 | | 7/2004 | Saito et al. | | |
| 2002/0110216 | A1 | | 8/2002 | Saito et al. | | |
| 2003/0226973 | A1 | * | 12/2003 | Beusch | .................. | 250/370.09 |
| 2004/0144926 | A1 | * | 7/2004 | Arques et al. | ......... | 250/370.01 |

FOREIGN PATENT DOCUMENTS

| EP | 0 444 869 A2 | 9/1991 |
| JP | 2001-242253 | 9/2001 |
| WO | WO 01/13140 A1 | 2/2001 |

\* cited by examiner

*Primary Examiner*—David Porta
*Assistant Examiner*—Djura Malevic
(74) *Attorney, Agent, or Firm*—Oblon, Spivak, McClelland, Maier & Neustadt, P.C.

(57) ABSTRACT

An X-ray CT apparatus 20 comprises an X-ray generating unit 22 and a radiation detector 23. The radiation detector 23 includes a plurality of detecting elements put in two-dimensional positions and separated into a plurality of readout blocks, a readout circuit for reading out electric signals from the detecting elements in the respective readout blocks, a switch circuit 26 for switching the electric signals read out to the readout circuit from the detecting elements at the readout blocks and a switch control circuit 27 for controlling the switch circuit 26 so as to read out electric signals with time-sharing from corresponding detecting elements in a common readout block of the readout blocks to the readout circuit and to read out corresponding electric signals in parallel from at least two of the detecting elements to the readout circuit, the two being in different readout blocks each other.

7 Claims, 16 Drawing Sheets

X-RAY CT APPARATUS, RADIATION DETECTOR AND METHOD FOR READING OUT ELECTRIC SIGNALS OF A RADIATION DETECTOR

BACKGROUND OF THE INVENTION

1. Field of the Invention

The present invention relates to an X-ray CT (computed tomography) apparatus which includes a plurality of detecting elements two-dimensionally arranged for detecting X-rays, time-divides electric signals from the detecting elements by a switch, and reads-out the time-divided signals, a radiation detector and a method for reading out electric signals of a radiation detector.

2. Description of the Related Art

Conventionally, an X-ray CT apparatus generates a tomographic image by irradiating a patient as a object with X-rays, detecting the transmitted X-rays, and visualizing the inside structure of the object (see, for example, JP-A-2001-242253).

In an X-ray CT apparatus for medical use, the object is irradiated from an X-ray tube with X-rays in various directions, the transmitted X-rays are absorbed by a radiation detector at the facing position in the case of sandwiching the object, and an electric signal is finally generated. The electric signal reflects the strength of the transmitted X-ray. A tomographic image of the object is subjected to reconstruction based on data of the obtained signal, and is displayed on a display device.

For example, in a third-generation X-ray CT apparatus, an X-ray tube and a radiation detector are rotated on the plane vertical to the body axis of the object, the transmitted X-ray with which the object is irradiated from the X-ray tube is detected by the radiation detector, and a detected X-ray detecting signal is transmitted to a data acquisition system, thereby acquiring data. One tomographic image on the rotation plane is reconstructed by the rotation for one period (180° or 360°) and is then displayed.

Therefore, the radiation detector comprises a large number of detector blocks which are densely arranged along an arc on the rotation plane. The detector blocks are connected to the data acquisition system. The detector block is, e.g., a two-dimensional photodiode array detector block in many cases.

FIG. 17 is a diagram schematically showing one conventional two-dimensional photodiode array detector block. FIG. 18 is a side view showing a conventional two-dimensional photodiode array detector block 1 shown in FIG. 17. A scintillator is not shown in FIG. 17.

The two-dimensional photodiode array detector block 1 comprises a plurality of detecting elements 3 on a substrate 2 in the column direction (channel direction C), serving as the rotating direction of a radiator detector, and in the row direction (slice direction A), serving as the body axis, so as to acquire data for a plurality of tomographs in the data acquisition for one period.

The detecting element 3 comprises a scintillator 4 and a photodiode (PD) 5. Generally, the number of scintillators 4 is equal to the number of photodiodes 5, the X-rays incident on the scintillator 4 are converted into visible light, and the light is converted into an electric signal by the photodiode 5. Further, the electric signal covered by the photodiode 5 is captured from one end of the slice direction A serving as the body axis or both ends and is then guided to a data acquisition system (not shown) so as to arrange a large number of two-dimensional photodiode array detector blocks 1 on the rotation plane of the radiation detector.

Therefore, the photodiodes 5 are connected to a plurality of integrators by wire-bonding 6, and the electric signals from the photodiodes 5 are transmitted to integrators 7. Further, the photodiodes 5 are connected to a common switch 8 such as an MUX (Multiplexer) by wire-bonding 6, and the switch 8 is connected to a circuit substrate 9, such as an FPC (flexible printed circuit), on the substrate 2.

All detecting elements 3 are connected to the data acquisition systems with a one-to-one correspondence, thereby reducing active areas S1 of the detecting elements 3. However, wiring areas S2 increase in size and thus are not mounted on the substrate 2 by wiring. That is, the number of wire bonds 6 is limited. Then, the electric signals from the photodiodes 5 are stored into the integrators 7, are time-divided by the switch 8 in the slice direction A, and are sequentially outputted to the circuit substrate 9 such as the FPC. Further, the circuit substrate 9 guides the electric signals to the data acquisition system.

In addition, the increase of the number of the detecting elements 3 prevents a sufficient space for the detecting elements 3 from being ensured under the restriction on the wiring area S2. Then, another two-dimensional photodiode array detector block is proposed by improving the wiring pattern.

FIG. 19 is a schematic diagram showing another conventional two-dimensional photodiode array detector block which is formed by improving the wiring pattern. A scintillator is not shown in FIG. 19.

Referring to FIG. 19, a two-dimensional photodiode array detector block 1A comprises a plurality of detecting elements 3 which are two-dimensionally arranged in the form of a matrix on the substrate 2. A transistor switch 10 is arranged at the output of the photodiode 5 of the detecting element 3. The photodiodes 5 on the single column are connected to a common signal line 11 via the transistor switch 10. The transistor switch 10 of the photodiodes 5 on the single column is connected to a common control line 12.

In the two-dimensional photodiode array detecting element block 1A, X-rays are incident on the scintillator (not shown) of the detecting element 3 and then are converted into light. Further, the photodiode 5 converts the light into an electric signal, and the electric signal is stored into the photodiode 5 as a charge. The control line 12 sequentially transmits a switch control signal to the transistor switches 10 in the row direction and thus the transistor switches 10 become active. The electric signals are time-divided in parallel with each other from the photodiodes 5 on the same row, and are sequentially time-divided in the row direction (slice direction A) from the photodiodes 5 on the same column. That is, both the electric signals from the photodiodes 5 are outputted to the signal lines 11 via the transistor switches 10.

That is, in the two-dimensional photodiode array detector block 1A shown in FIG. 19, the transistor switches 10 are individually arranged at the photodiodes 5 and the signal lines 11 are commonly used, thereby reducing the number of signal lines 11.

FIG. 20 is a diagram showing a connecting method of the detecting elements 3 and a readout circuit in the conventional two-dimensional photodiode array detector block 1,1A. FIG. 21 is a schematic diagram showing a readout time of the electric signal from the conventional detecting elements 3 shown in FIG. 20.

The electric signals are outputted by the two-dimensional photodiode array detector block 1 or two-dimensional photodiode array detector block 1A in FIG. 17 or 19 having the detecting elements 3 corresponding to 16 rows, as shown in FIG. 20. One column is focused and then the electric signals from the detecting elements 3 are time-divided via a common integral amplifier 13. After that, the time-divided signals are A/D converted by an A/D converter 14 and are read-out by a readout circuit. Referring to FIG. 21, the readout time is used as the axis and then electric signals D from the 16 detecting elements 3 are sequentially read-out in row order by the readout circuit via the integral amplifier 13.

Then, the electric signals which are time-divided and read-out in parallel with each other in the row direction (slice direction A) from the detecting elements 3 of the column are transmitted to an image reconstructing unit via a circuit substrate and a data acquisition system. Further, the image reconstructing unit reconstructs a tomographic image of a object.

In the conventional two-dimensional photodiode array detector blocks 1 and 1A, the electric signals are time-divided depending on the number of rows of the detecting elements 3. Therefore, as the number of rows of the detecting element 3 is larger, it takes a longer time for reading-out the electric signals from the detecting elements 3 on all rows.

In particular, the integral amplifier 13 stores the electric signals from the detecting elements 3 as charges for a predetermined time for the purpose of integration. Therefore, the readout time of the electric signals from the detecting elements 3 is longer, mainly depending on the storing time of charges in the integral amplifier 13.

However, the time for reading-out the electric signals from the detecting elements 3 in the two-dimensional photodiode array detector block is generally limited to within a predetermined time. As the number of detecting elements increases for a predetermined readout-time of the electric signals, the readout time of the electric signals per row is shorter in accordance with the increased number of rows of the detecting element, that is, the electric signals need to be read-out faster.

If the radiation detector acquires the data 900 times per second, the data needs to be acquired once in a time of 1.111 ms. Since the number of rows of the detecting element is 16, the electric signals need to be read-out from the detecting elements corresponding to the 16 rows for a time of 1.111 ms, and the readout speed per row is thus 0.069 ms.

In accordance with the increase in readout speed of the electric signals, the readout circuit of the electric signal is not operated in the two-dimensional photodiode array detector block. Further, not only does the noise increase but also the image quality of the tomographic image generated by the above-obtained electric signal deteriorates. In other words, the number of rows of the detecting element arranged on the substrate of the two-dimensional photodiode array detector block is restricted.

SUMMARY OF THE INVENTION

The present invention is devised to solve the conventional problems. It is an object of the present invention to provide an X-ray CT apparatus, a radiation detector and a method for reading out electric signals of a radiation detector in which the circuit design is simplified and the noise of electric signals is reduced by decreasing the demanded readout speed of the electric signals readout from the detecting elements.

In an aspect, to achieve the object, the present invention provides an X-ray CT apparatus comprising an X-ray generating unit for irradiating an X-ray to an object and a radiation detector for detecting the X-ray transmitted the object, wherein the radiation detector includes a plurality of detecting elements put in two-dimensional positions and separated into a plurality of readout blocks, a readout circuit for reading out electric signals from the detecting elements in the respective readout blocks, a switch circuit for switching the electric signals read out to the readout circuit from the detecting elements at the readout blocks and a switch control circuit for controlling the switch circuit so as to read out electric signals with time-sharing from corresponding detecting elements in a common readout block of the readout blocks to the readout circuit and to read out corresponding electric signals in parallel from at least two of the detecting elements to the readout circuit, the two being in different readout blocks each other.

Furthermore, in an aspect, to achieve the object, the present invention provides an X-ray CT apparatus comprising an X-ray generating unit for irradiating an X-ray to an object, a radiation detector for detecting the X-ray transmitted the object and a data acquisition system for accumulating X-ray detected data detected to the radiation detector with an analog-to-digital converter wherein the radiation detector includes a plurality of detecting elements put in two-dimensional positions and separated into a plurality of readout blocks, an integral amplifier for accumulating electric charges from the detecting elements and reading out electric signals from the detecting elements in the respective readout blocks, a selector for selecting an electric signal to output to the analog-to-digital converter from the electric signals read out with the integral amplifier, a switch circuit for switching the electric signals read out to the integral amplifier from the detecting elements at the readout blocks and a switch control circuit for controlling the switch circuit so as to read out electric signals with time-sharing from corresponding detecting elements in a common readout block of the readout blocks to the integral amplifiers and to read out corresponding electric signals in parallel from at least two of the detecting elements to the integral amplifiers, the two being in different readout blocks each other.

Furthermore, in an aspect, to achieve the object, the present invention provides a radiation detector comprising a plurality of detecting elements put in two-dimensional positions and separated into a plurality of readout blocks, a readout circuit for reading out electric signals from the detecting elements in the respective readout blocks, a switch circuit for switching the electric signals read out to the readout circuit from the detecting elements at the readout blocks and a switch control circuit for controlling the switch circuit so as to read out electric signals with time-sharing from corresponding detecting elements in a common readout block of the readout blocks to the readout circuit and to read out corresponding electric signals in parallel from at least two of the detecting elements to the readout circuit, the two being in different readout blocks each other.

Furthermore, in an aspect, to achieve the object, the present invention provides a radiation detector comprising a plurality of detecting elements put in two-dimensional positions and separated into a plurality of readout blocks, an integral amplifier for accumulating electric charges from the detecting elements and reading out electric signals from the detecting elements in the respective readout blocks, a selector for selecting an electric signal ought to output to an analog-to-digital converter from the electric signals read out with the integral amplifier, a switch circuit for switching the electric signals read out to the integral amplifier from the detecting elements at the readout blocks and a switch control circuit for controlling the switch circuit so as to read out electric signals with time-sharing from corresponding detecting elements in a common readout block of the readout blocks to the integral amplifiers and to read out corresponding electric signals in parallel from at least two of the detecting elements to the integral amplifiers, the two being in different readout blocks each other.

Furthermore, in an aspect, to achieve the object, the present invention provides a method for reading out electric signals of a radiation detector comprising separating a plurality of detecting elements put in two-dimensional positions to a plurality of readout blocks and reading out electric signals with time-sharing from corresponding detecting elements in a common readout block of the readout blocks, and reading out corresponding electric signals in parallel from at least two of the detecting elements, the two being in the different readout blocks each other.

With the X-ray CT apparatus, the radiation detector and the method for reading out electric signals of the radiation detector as described above, it is possible to simplify the circuit design and reduce the noise of electric signals by decreasing the demanded readout speed of the electric signals read-out from the detecting elements.

DESCRIPTION OF THE PREFERRED EMBODIMENTS

An X-ray CT apparatus, a radiation detector and a method for reading out electric signals of a radiation detector according to embodiments of the present invention will be described with reference to the accompanying drawings.

Figure 1:
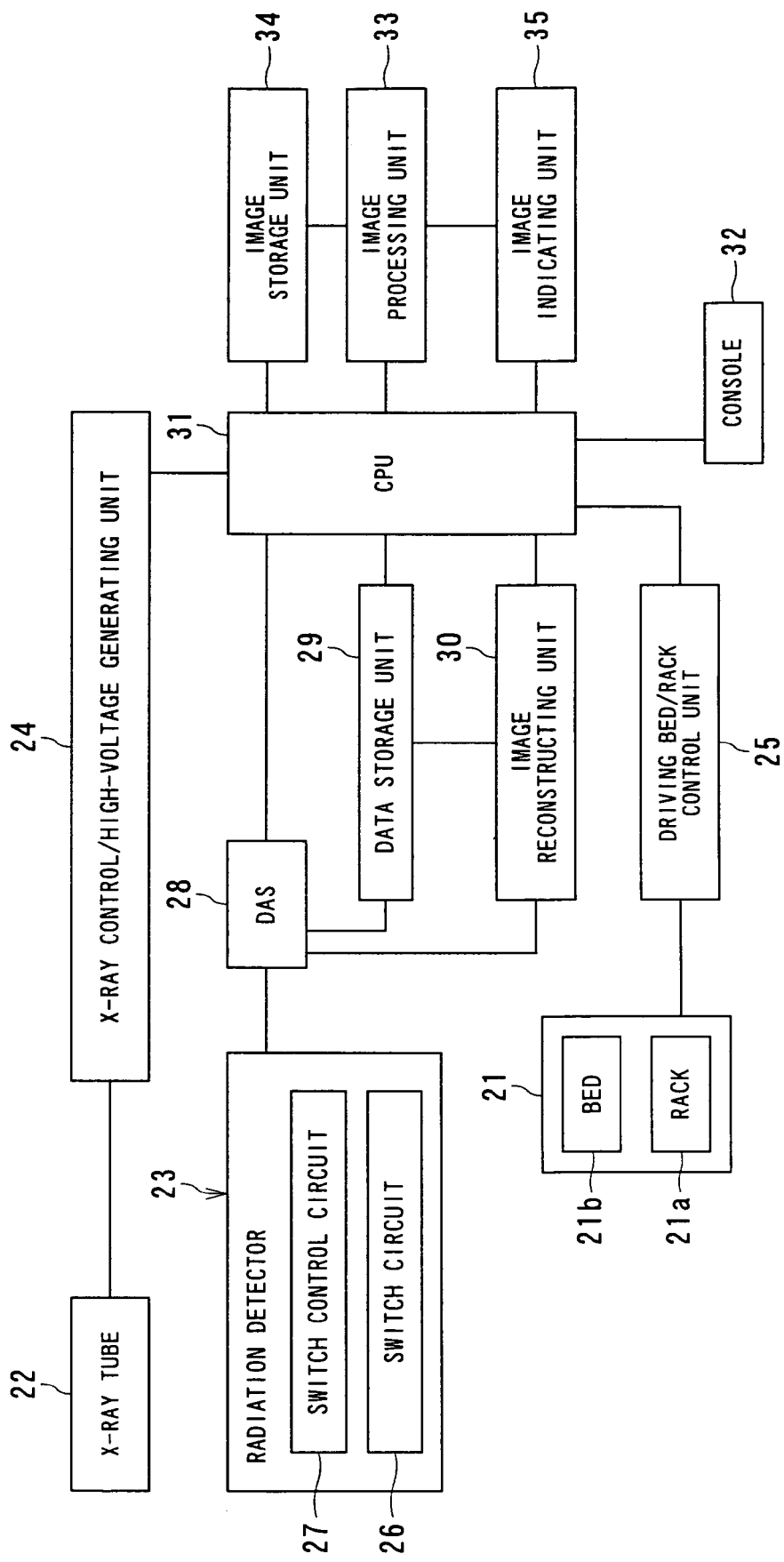
FIG. 1 is a block diagram showing an X-ray CT apparatus according to a first embodiment of the present invention.

FIG. 1 is a block diagram showing an X-ray CT apparatus according to a first embodiment of the present invention.

An X-ray CT apparatus 20 comprises a rack 21a, a bed 21b, an X-ray tube 22, and a radiation detector 23 as an X-ray generating unit. The bed 21b is sandwiched by the X-ray tube 22 on one side and radiation detector 23 on the other side. The X-ray tube 22 faces the radiation detector 23 on the rack 21a. A imaging area is between the X-ray tube 22 and the radiation detector 23, and a object (not shown) is set onto the bed 21b.

The X-ray tube 22 is connected to an X-ray control/high-voltage generating unit 24. The X-ray control/high-voltage generating unit 24 has a function for controlling the X-ray tube 22 by applying predetermined electric power to the X-ray tube 22.

A bed/rack 21 is connected to a driving bed/rack control unit 25. The driving bed/rack control unit 25 has a function for controlling the position of the bed/rack 21 by applying a control signal to the bed/rack 21.

The radiation detector 23 having a plurality of detecting elements comprises a switch circuit 26 for switching the electric signal read-out from the detecting elements and a switch control circuit 27 for controlling the switch circuit 26. The radiation detector 23 is connected to a data acquisition system (DAS) 28, and a data storage unit 29 is connected to the data acquisition system 28. Further, the data acquisition system 28 and the data storage unit 29 are connected to an image reconstructing unit 30.

The radiation detector 23 has a function for detecting the X-rays transmitted through the object from the X-ray tube 22 by using the detecting elements and transmitting the detected X-rays as the electric signal to the data acquisition system 28.

The data acquisition system 28 has a function for converting the electric signal transmitted from the radiation detector 23 into a digital signal, a function for generating X-ray detection data through various necessary processing, a function for writing the generated X-ray detection data to the data storage unit 29, and a function for transmitting the X-ray detection data to the image reconstructing unit 30.

The image reconstructing unit 30 has a function for generating image data of the object by performing image reconstruction processing to the X-ray detection data received from the data acquisition system 28 or the X-ray detection data which is read from the data storage unit 29.

Further, the data acquisition system 28, the data storage unit 29, the image reconstructing unit 30, the driving bed/rack control unit 25, and the X-ray control/high-voltage generating unit 24 are connected to a central processing unit (hereinafter, referred to as a CPU) 31. Connected to the CPU 31 are a console 32, an image processing unit 33, an image storage unit 34, and an image indicating unit 35.

Various programs are read, in advance, into the CPU 31. Further, the CPU 31 has a function for applying a control signal, in accordance with operation information from the console 32, to control the driving bed/rack control unit 25 and the X-ray control/high-voltage generating unit 24, and a function for receiving the image data or the X-ray detection data from the data acquisition system 28, the data storage unit 29, and the image reconstructing unit 30, performing various data-processing, and then recording the processed data to the data storage unit 29 and the image storage unit 34 or transmitting the data to the image processing unit 33 and the image indicating unit 35.

The image processing unit 33 has a function for receiving the image data from the CPU 31, performing various image-processing of the received data, and then recording the data to the image storage unit 34 or transmitting the data and displaying the data onto the image indicating unit 35.

Figure 2:
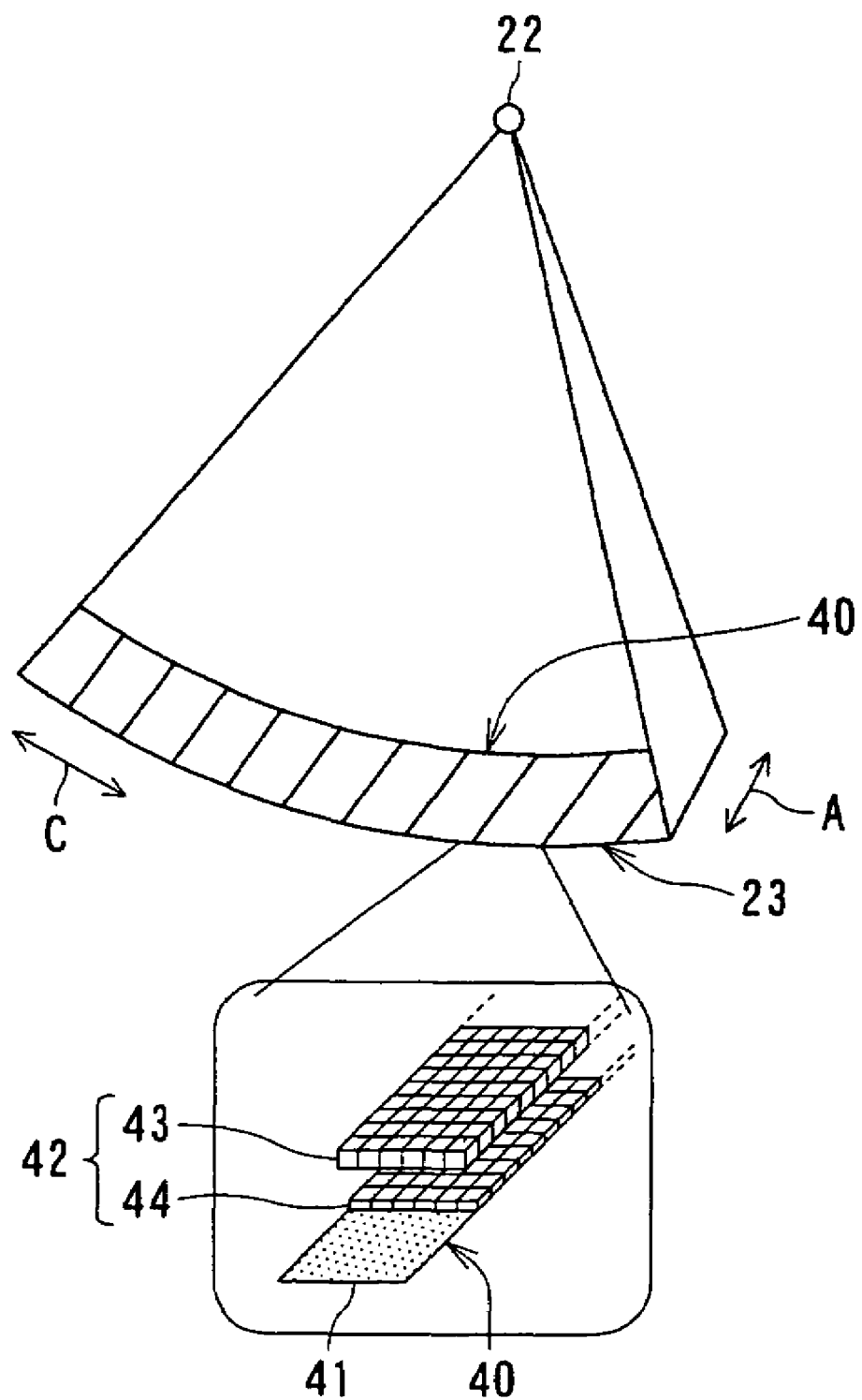
FIG. 2 is a schematic diagram showing the X-ray tube and the radiation detector in the X-ray CT apparatus 20 shown in FIG. 1.
Figure 3:
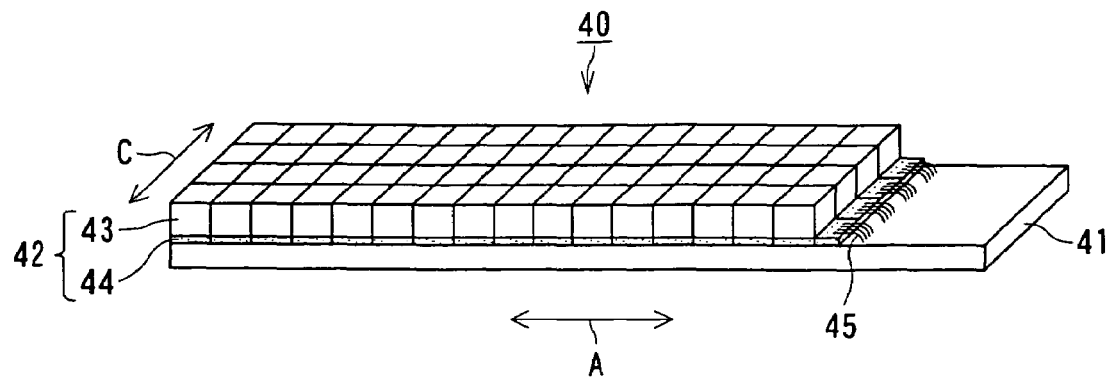
FIG. 3 is an oblique perspective view schematically showing the structure of a two-dimensional photodiode array detector block shown in FIG. 2.
Figure 4:
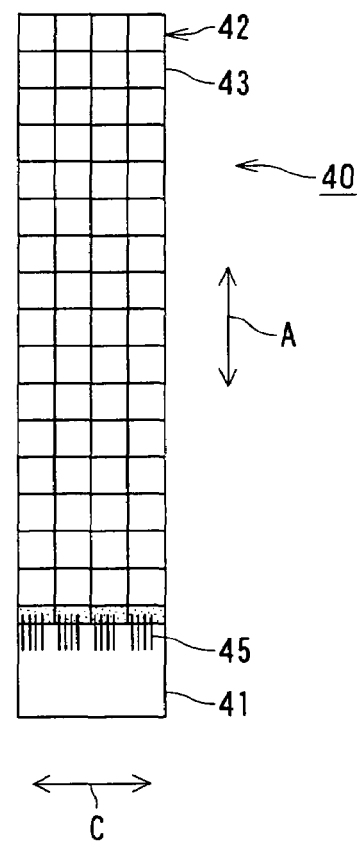
FIG. 4 is a top surface view showing the two-dimensional photodiode array detector block shown in FIG. 3.

FIG. 2 is a schematic diagram showing the X-ray tube 22 and the radiation detector 23 in the X-ray CT apparatus 20 shown in FIG. 1. FIG. 3 is an oblique perspective view schematically showing the structure of a two-dimensional photodiode array detector block shown in FIG. 2. FIG. 4 is a top surface view showing the two-dimensional photodiode array detector block shown in FIG. 3.

The X-ray tube 22 and the radiation detector 23 face each other and further are arranged in the position where they can rotate in a channel direction C on the plane nearby vertical to a body axis direction (slice direction A) of the object. The radiation detector 23 comprises a large number of two-dimensional photodiode array detector blocks 40 which are densely arranged along an arc in the rotating direction. The two-dimensional photodiode array detector blocks 40 are connected to the data acquisition system 28 shown in FIG. 1.

In the two-dimensional photodiode array detector block 40, a plurality of detecting elements 42 are arranged in the channel direction C and the slice direction A on a substrate 41 such as a printed circuit board (hereinafter, referred to as a PCB). FIGS. 3 and 4 show an example of the two-dimensional photodiode array detector block 40 comprising the detecting elements 42 corresponding to 16 rows in the slice direction A. In the example shown in FIGS. 3 and 4, the detecting elements 42 in the channel direction C correspond to four columns, for the purpose of easy understanding.

The detecting element 42 comprises a scintillator 43 and a photodiode 44, and has a function for detecting the X-rays and converting the detected X-rays into the electric signal. Generally, the element-number of the scintillators 43 is equal to that of the photodiodes 44. The scintillator 43 has a function for converting the X-rays incident on the detecting elements 42 into light and transmitting the light to the photodiode 44. The photodiode 44 has a function for converting the light received from the scintillator 43 into the electric signal.

The electric signal converted by the photodiode 44 needs to be captured from one direction of the body-axis direction or both directions and to be guided to the data acquisition system 28 so as to arrange a larger number of detector blocks in the rotating direction of the radiation detector 23. Therefore, the photodiode 44 is connected to a readout circuit on the substrate 41 by connecting means such as a wire bond 45.

However, when the number of detecting elements 42 is large and then all detecting elements 42 are connected to the data acquisition systems 28 with a one-to-one correspondence, active areas of the detecting elements 42 are reduced in size and wiring areas thereof are increased in size, thereby preventing mounting on the substrate 41 by wiring. Then, the two-dimensional photodiode array detector block 40 comprises, at an arbitrary position thereof, the switch circuit 26 for switching the electric signal read-out from the detecting elements 42 by an arbitrary wiring pattern and the switch control circuit 27 for controlling the switch circuit 26.

The detecting element 42 for reading-out the electric signal is switched under the control operation by applying the switch control signal to the switch circuit 26 from the switch control circuit 27. That is, the electric signals from the plurality of detecting elements 42 are time-shared by the switch circuit 26 and are guided to a common readout circuit.

The switch control circuit 27 may be arranged outside the detector block.

Figure 5:
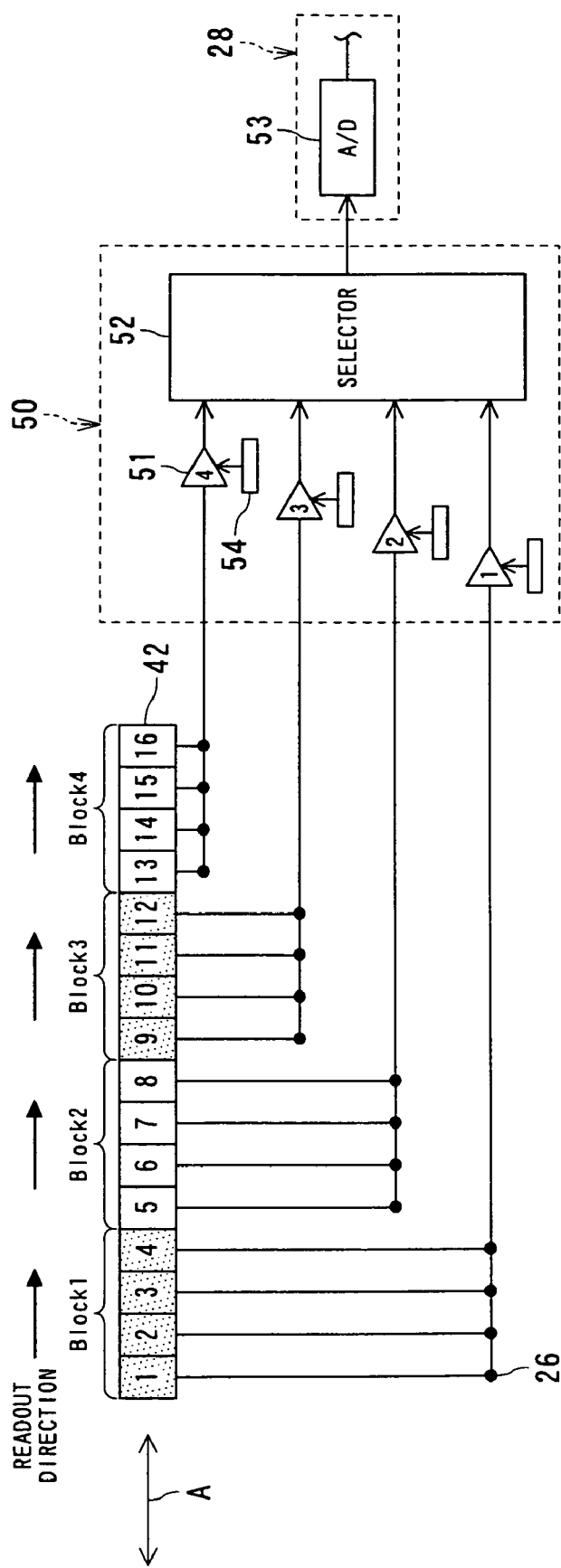
FIG. 5 is a conceptual diagram showing a connecting method of the detecting elements and the readout circuit in the two-dimensional photodiode array detector block shown in FIG. 2.
Figure 6:
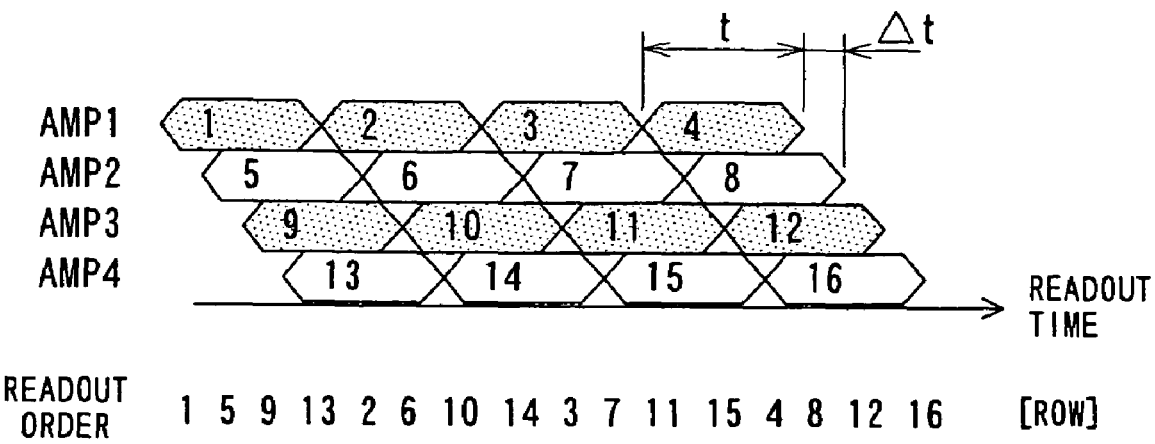
FIG. 6 is a schematic diagram showing the readout time of the electric signals from the detecting elements by integral amplifiers shown in FIG. 5.

FIG. 5 is a conceptual diagram showing a connecting method of the detecting elements 42 and the readout circuit in the two-dimensional photodiode array detector block 40 shown in FIG. 2. FIG. 6 is a schematic diagram showing the readout time of the electric signals from the detecting elements 42 by integral amplifiers 51 shown in FIG. 5.

In the two-dimensional photodiode array detector block 40, the detecting elements 42, serving as the target of time sharing of the read-out electric signals, are divided into a plurality of readout blocks, and the detecting elements 42 are connected to a readout circuit 50. Further, the readout circuit 50 is connected to the data acquisition system 28.

The readout circuit 50 comprises a plurality of integral amplifiers 51 in accordance with the number of readout blocks, and a selector 52. The data acquisition system 28 comprises an A/D converter 53. The detecting elements 42 in the single readout block are connected to the common integral amplifiers 51. Further, the integral amplifiers 51 are connected to the common selector 52, and the selector 52 is connected to the A/D converter 53 of the data acquisition system 28. The integral amplifiers 51 have amplifier controllers 54.

In the two-dimensional photodiode array detector block 40, the electric signals are time-shared for readout operation every column in the row direction. Here, the detecting elements 42 are divided into a plurality of readout blocks in one column in the row direction.

Referring to FIG. 5, in the two-dimensional photodiode array detector block 40 having the detecting elements 42 corresponding to 16 rows, the detecting elements 42 are divided into four readout blocks (block 1, block 2, block 3, and block 4) in the row direction, and the detecting elements 42 divided into the four readout blocks are connected to four integral amplifiers 51 (AMP 1, AMP 2, AMP 3, and AMP 4), respectively.

The electric signals read-out from the detecting elements 42 in the single readout-block can be switched by the switch circuit 26. The integral amplifiers 51 of the readout circuit 50 connected to the readout blocks can be operated in parallel, respectively. In the respective readout blocks, the electric signals are read-out to the integral amplifiers 51 in the constant readout direction in row order from the detecting elements 42 by the switching operation of the switch circuit 26, as shown in FIG. 5.

The integral amplifiers 51 store the charges for amplifying the electric signals from the detecting elements 42. A predetermined amount of charge is stored and then the electric signals are outputted to the selector 52. In the selector 52, the electric signals received from the integral amplifiers 51 are switched and then are sequentially outputted to the A/D converter 53 in the data acquisition system 28. Further, in the A/D converter 53 of the data acquisition system 28, the electric signals received from the detecting elements 42 are sequentially converted into digital signals and then are outputted to a subsequent circuit in the readout circuit 50.

When the electric signals are outputted to the selector 52 from the integral amplifiers 51, the amplifier controller 54 clears (initializes) the charges stored in the integral amplifiers 51 at an arbitrary timing to additionally store the charges in the integral amplifiers 51. Therefore, if the charge stored in one integral amplifier 51 is cleared at the timing for storing the charge from the single detecting-element 42 in the integral amplifier 51, the electric signals are generated from the individual detecting elements 42. If the charge stored in one integral amplifier 51 are cleared at the timing for storing the charges from the plurality of detecting elements 42 in the integral amplifier 51, one electric signal is generated in response to the stored charges from the plurality of detecting elements 42.

Although the switch circuit 26 may be arranged at each of the detecting elements 42, the switch circuit 26 may be arranged at an arbitrary position separated from the detecting elements 42, having a switching function of the detecting elements 42. Referring to FIG. 5, conceptually, the switch circuits 26 are arranged at each of the detecting elements 42 for the purpose of easy understanding.

The horizontal axis in FIG. 6 shows the readout time of the electric signal. Referring to FIG. 6, the electric signals (1 to 16) from the detecting elements 42 in the rows are sequentially switched by the switch circuits 26 every readout block (block 1, block 2, block 3, and block 4), and the integral amplifiers 51 (AMP 1, AMP 2, AMP 3, and AMP 4) readout the electric signals. That is, the integral amplifier 51 (AMP 1) connected to the detecting elements 42 in block 1 sequentially reads-out the electric signals from the detecting elements 42 in four rows including row 1, row 2, row 3, and row 4.

Further, the integral amplifier 51 (AMP 2) connected to the detecting elements 42 in the block 2 sequentially reads-out the electric signals from the detecting elements 42 in four rows including row 5, row 6, row 7, and row 8. The foregoing can be applied to block 3 and block 4.

The switch control signal applied to the switch circuit 26 from the switch control circuit 27 adjusts the readout time of the electric signals by the integral amplifier 51 from the detecting elements 42 every readout block.

The electric signals read-out by the integral amplifiers 51 are converted into digital signals by the A/D converter 53 in the data acquisition system 28 via the subsequent selector 52. Since the A/D converter 53 is commonly arranged to the plurality of integral amplifiers 51, the electric signals from the integral amplifiers 51 are sequentially outputted to the A/D converter 53. Therefore, the electric signals need to be outputted to the common A/D converter 53 from the integral amplifiers 51 with the time delay so that the A/D converter 53 sequentially converts the electric signals into the digital signals.

Foe example, the readout time of the electric signals from the detecting elements 42 in the row 5 to be first read-out in the block 2 is set between the readout time of the electric signals from the detecting elements 42 in row 1 to be first read-out in block 1 and the readout time of the electric signals from the detecting elements 42 in row 2 to be next read-out in block 2. Then, a time delay $\Delta t$ necessary for at least reading-out the electric signals by the A/D converter 53 can be ensured.

In this case, the time delay $\Delta t$ necessary for at least reading-out the electric signals by the A/D converter 53 is shorter than a time t necessary for storing the charges by the integral amplifiers 51. The charges are stored partly in parallel in the integral amplifiers 51. Thus, the readout time of the electric signals is reduced in view of the entire readout circuit 50.

Similarly, the readout times of the electric signals in block 3 and block 4 are shifted, thereby reading-out the electric signals in the row direction from the column of the two-dimensional photodiode array detector block 40 shown in FIG. 5 in the readout order of row 1, row 5, row 9, row 13, row 2, . . . , and row 16, as shown in FIG. 6.

Here, the charges stored in the integral amplifier 51 are cleared at readout timings of the electric signals to the integral amplifier 51 from the single detecting-element 42. Further, when the electric signals from the plurality of adjacent detecting elements 42 are read-out to the integral amplifier 51, the charges stored in the integral amplifier 51 may be cleared. The amplifier controller 54 controls the timing for clearing the charges stored in the integral amplifiers 51, as mentioned above.

When the electric signals from the plurality of adjacent detecting elements 42 are read-out to the integral amplifier 51 and then the integral amplifier 51 outputs the electric signals to the A/D converter 53 and the charges stored in the integral amplifier 51 are cleared, the electric signals can be read-out at the timing in accordance with the slice thickness. That is, when generating one electric signal based on the charges from the plurality of adjacent detecting elements 42 in the slice direction A, the X-ray detection data with the slice thickness in accordance with the number of the detecting elements 42 can be acquired.

For example, upon acquiring the X-ray detection data with a slice thickness of 0.5 mm from the single detecting-element 42, the electric signal is outputted to the A/D converter 53 at the timing for storing the charges from the adjacent two detecting elements 42 in the slice direction A to the integral amplifier 51 and then the charges stored in the integral amplifier 51 are cleared, thereby acquiring the X-ray detection data with a slice thickness of 1 mm.

Figure 7:
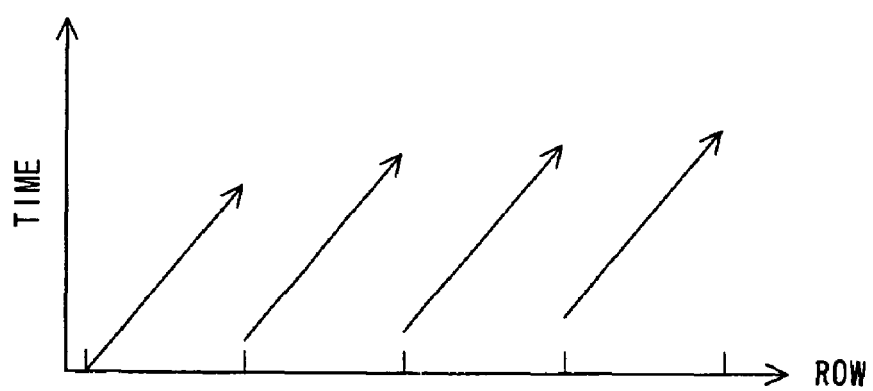
FIG. 7 is a diagram showing a relationship between the row and the time upon reading-out the electric signals from the detecting elements shown in FIG. 5.

FIG. 7 is a diagram showing a relationship between the row and the time upon reading-out the electric signals from the detecting elements 42 shown in FIG. 5.

Referring to FIG. 7, the vertical axis shows the readout time of the electric signals, and the horizontal axis shows the row of the detecting elements 42 for reading-out the electric signals. The detecting elements 42 are divided into readout blocks in the row direction and are operated in parallel every readout block. Therefore, the number of upper-right straight lines for increasing the rows in accordance with the time corresponds to the number of the readout blocks, as shown in FIG. 7. Further, since the readout time is shifted every readout block, the straight lines are shifted in the time direction in accordance with the readout block.

Figure 8:
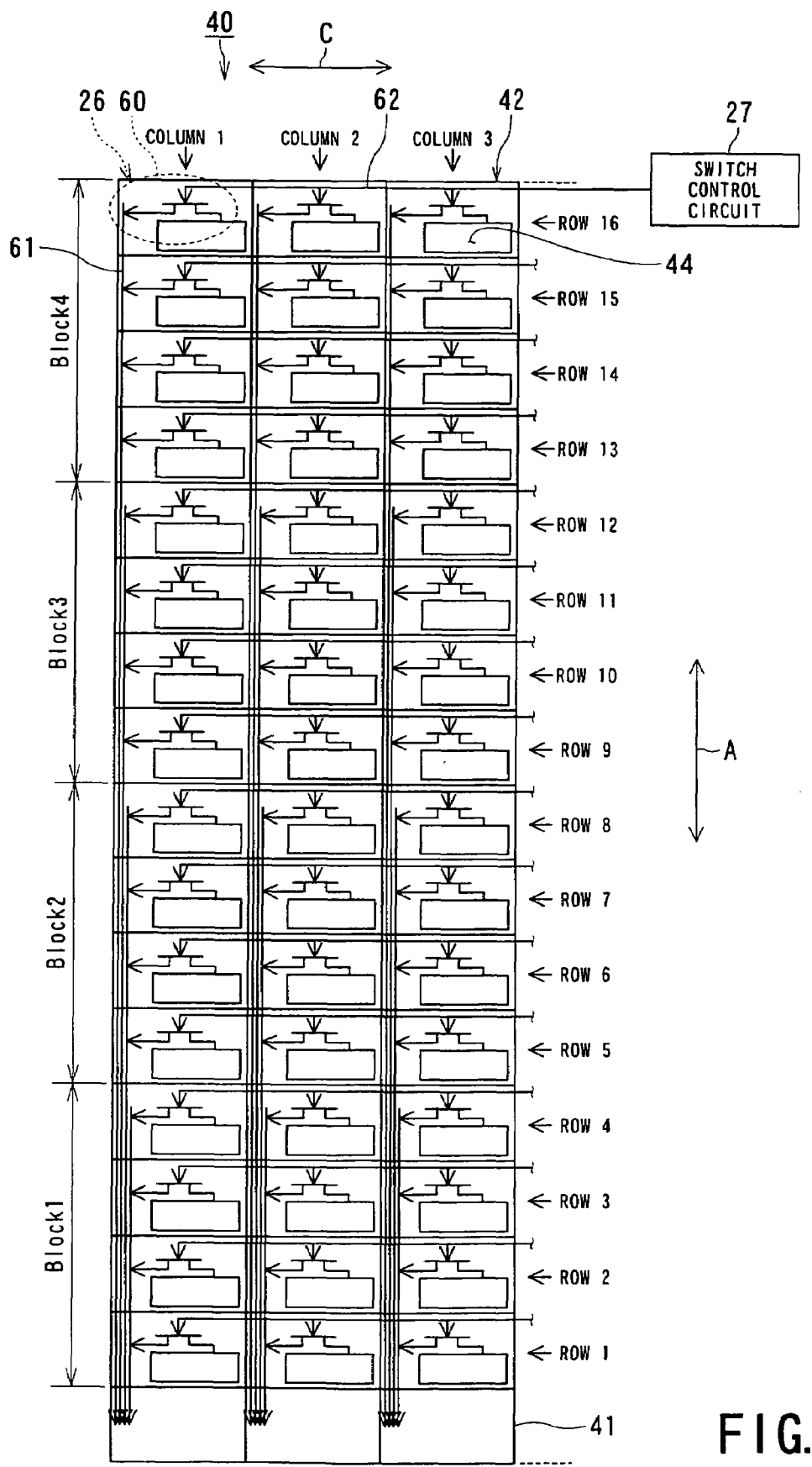
FIG. 8 is a schematic diagram showing one example of the circuit structure of the switch circuit arranged at the two-dimensional photodiode array detector block shown in FIG. 3.

FIG. 8 is a schematic diagram showing one example of the circuit structure of the switch circuit 26 arranged at the two-dimensional photodiode array detector block 40 shown in FIG. 3. The scintillator 43 is not shown in FIG. 7.

Referring to FIG. 7, the two-dimensional photodiode array detector block 40 comprises a plurality of detecting elements 42 which are arranged in the form of a two-dimensional matrix on the substrate 41 for example. Referring to FIG. 8, the two-dimensional photodiode array detector block 40 has the detecting elements 42 corresponding to 16 rows in the slice direction A, and the number of columns of the detecting elements 42 in the channel direction C is 3 for the purpose of easy understanding.

In the two-dimensional photodiode array detector block 40, transistor switches 60 as the switch circuits 26 are individually arranged at the output side of the photodiodes 44 of the detecting elements 42. Further, the detecting elements 42 are divided into a plurality of readout blocks, e.g., four readout blocks (block 1, block 2, block 3, and block 4) in the slice direction A every four rows. The photodiodes 44 in the single column in the common readout block are connected to a common signal line 61 via the transistor switch 60, and the transistor switches 60 of the photodiodes 44 in the single row are connected to a common control line 62.

The control lines 62 are connected to the switch control circuit 27. The switch control circuit 27 has a function for setting, to be active, the transistor switches 60 in the single column connected to the common control line 62 at an arbitrary timing by applying the switch control signal to the transistor switches 60 forming the switch circuit 26 via the control lines 62. Therefore, the switch control signals are applied to the plurality of control lines 62 in the different readout blocks to set, to be active, the switch circuits 26 in a plurality of rows and columns. The transistor switches 60 in the different readout blocks are operated in parallel to simultaneously read-out the electric signals from the photodiodes 44 in the plurality of rows and columns. Further, under the control operation of the timing of the switch control signal, the electric signals from the photodiodes 44 in the common readout block are time-shared in the row direction.

The circuit structure of the switch circuit 26 arranged to the two-dimensional photodiode array detector block 40 is not limited to the circuit pattern shown in FIG. 8 and may be structured by combining an integrator and a switch such as an MUX (multiplexer), similarly to the conventional two-dimensional photodiode array detector block 1.

Next, the operation of the X-ray CT apparatus 20 will be described.

First, the object (not shown) is set on the bed 21b. Operation information inputted to the console 32 is transmitted to the CPU 31, various programs that are read in advance to the CPU 31 are executed, and the control signal is transmitted to the driving bed/rack control unit 25 and the X-ray control/high-voltage generating unit 24. That is, the control signal from the CPU 31 controls the driving bed/rack control unit 25 and the X-ray control/high-voltage generating unit 24, the bed 21b is driven to the position designated by the console 32, and the object irradiated from the X-ray tube 22 with the X-ray under the designated condition.

The X-rays with which the object is irradiated are transmitted through the object and are incident on the two-dimensional photodiode array detector block 40 of the radiation detector 23 shown in FIG. 2. That is, the X-rays transmitted through the object are incident on the scintillator 43 of the plurality of detecting elements 42 two-dimensionally arranged in the slice direction A and the channel direction C on the substrate 41 of the two-dimensional photodiode array detector block 40 shown in FIG. 3, 4, or 8.

The scintillator 43 converts the incident X-rays into light and transmits the light to the photodiode 44. The photodiode 44 converts the light received from the scintillator 43 into the electric signal. In the case of the two-dimensional photodiode array detector block 40 shown in FIG. 8, the converted electric signals are temporarily stored, as charges, in the photodiode 44.

The switch control circuit 27 transmits the switch control signal, via the control line 62, to the transistor switch 60 in the row of the readout circuit 50 in the readout blocks with predetermined delay time. For example, the switch control circuit 27 sequentially transmits the switch control signals to the transistor switches 60 in row 1, row 5, row 9, and row 13 of block 1, block 2, block 3, and block 4, thereby setting the transistor switches 60 to be active.

In this case, the delay time of the switch control signals transmitted to the transistor switches 60 in the different readout blocks is set to the time delay $\Delta t$ necessary for reading-out the electric signals by the A/D converter 53.

As a result, the electric signals are sequentially read-out from the photodiodes 44 in row 1, row 5, row 9, and row 13.

The switch control circuit 27 transmits the switch control signals via the control line 62, with a predetermined delay time, to the transistor switches 60 in the row adjacent to the row from which the electric signals end to be read-out in the readout blocks, namely, the transistor switches 60 in row 2, row 6, row 10, and row 14.

In this case, the delay time of the switch control signals transmitted to the transistor switches 60 in the common readout block can be set to the entire time t necessary for storing the charges in the integral amplifiers 51.

Further, under the control operation of the transistor switches 60 by the switch control signal from the switch control circuit 27, the transistor switches 60 in the readout blocks are operated in parallel. Thus, the electric signals are read-out to the integral amplifiers 51 from the photodiodes 44 in the readout order shown in FIG. 6. That is, the time-shared electric signals are sequentially read-out from the photodiodes 44 in the common readout block to the integral amplifiers 51 via the signal line 61. And the electric signals are readout in partially parallel with the shift of the readout time from the photodiodes 44 in the different readout blocks to the integral amplifiers 51 via the signal line 61.

That is, four integral amplifiers 51 (AMPs) share and read-out the electric signals from the photodiodes 44 corresponding to 16 rows. Therefore, the data corresponding to 4 rows for one integral amplifier 51 (AMP) may be acquired one time. If the radiation detector 23 acquires the data 900 times per sec, the data corresponding to one time needs to be acquired during a time of 1.111 ms. Therefore, the electric signals need to be read-out from the detecting elements 42 corresponding to 4 rows during a time of 1.111 ms for one integral amplifier 51 (AMP), and the readout speed per row is 0.069 ms.

That is, the radiation detector 23 having the two-dimensional photodiode array detector block 40 shown in FIG. 5 or 8 has the readout speed of the electric signals as the X-ray detecting signals, which is reduced as compared with the readout speed of the electric signals of the radiation detectors having the conventional two-dimensional photodiode array detector blocks 1 and 1A.

In the radiation detector 23 having the two-dimensional photodiode array detector block 40 shown in FIG. 5 or 8, the plurality of photodiodes 44 in the common readout block are connected to the common signal line 61 via the transistor switches 60. Therefore, the number of signal lines 61 is reduced, a reduction in active area and an increase in wiring area of the detecting elements 42 are suppressed, and the mounting and wiring on the substrate are simplified. As a result, the noise of the electric signals is reduced.

As mentioned above, the electric signals read-out from the photodiodes 44 under the control operation of the transistor switches 60 are transmitted to the integral amplifiers 51 arranged at the readout circuit 50 on the substrate 41 by the wire-bonding 45.

The integral amplifiers 51 store the charges of the electric signals read-out from the photodiodes 44 in the readout blocks. By the operation of the selector 52, the integral amplifiers 51 sequentially output, to the A/D converter 53 in the data acquisition system 28 shown in FIG. 1, the electric signals as the X-ray detecting signals outputted from the radiation detector 23 in the predetermined readout order.

In the data acquisition system 28, the A/D converter 53 converts the electric signals received from the radiation detector 23 into the digital signals, and the X-ray detection data is generated by various necessary processing operations. The X-ray detection data is acquired on the rotation plane by rotation for one period (about 180° or about 360°). The acquired X-ray detection data is written and is stored to the data storage unit 29.

Further, the image reconstructing unit 30 receives the X-ray detection data from the data acquisition system 28, or reads-out the X-ray detection data from the data storage unit 29, and then performs the image reconstruction processing, thereby reconstructing the image data of the object. The reconstructed image data is transmitted to the CPU 31, and the CPU 31 performs various data processing operations of the image data and records the data to the image storage unit 34. If necessary, the image processing unit 33 performs various types of imaging processing on the image data.

The finally-generated image data indicating the tomographic image of the object is transmitted and is displayed on the image indicating unit 35. The noise in the electric signals used for generating the image data is reduced by reducing the number of the signal lines 61 in the radiation detector 23 and by simplifying the mounting on the substrate 41 to reduce the degradation of image quality.

Next, a description will be given of the X-ray CT apparatus 20 according to a modified example.

In the two-dimensional photodiode array detector block 40 in which the detecting elements 42 are connected to the common integral amplifier 51 by the switch circuits 26 for every readout block, as shown in FIG. 5, referring to FIG. 6, the readout order of the electric signals from the detecting elements 42 in the readout blocks has the same row-order, that is, the electric signals from the rows nearer the integral amplifiers 51 are read-out priorly and then there is a long time-delay between the readout times of the electric signals from the detecting elements 42 in the adjacent rows.

For example, when the detecting elements 42 corresponding to 16 rows are divided into four readout blocks (block 1, block 2, block 3, and block 4) for 4 rows, the time delay between the readout time of row 1, row 5, row 9, and row 13, which are first read-out in the readout blocks, and the readout time of row 4, row 8, row 12, and row 16, which are last read-out in the readout block is a time (1.111 ms) corresponding to approximately one view.

Therefore, the readout times in the adjacent rows (rows 4 and 5, rows 8 and 9, and rows 12 and 13) are shifted by approximately one sampling period. Thus, it is dangerous to deteriorate the image quality due to the generation of the image data from the electric signals acquired by the above sampling.

In order to solve the above-mentioned problem, the readout direction of the electric signals from the detecting elements 42 in the rows in the single readout block, namely, the readout order, can be adjusted to reduce the difference between the readout times of the electric signals from the detecting elements 42 in the adjacent rows. The switch control circuit 27 may have a function for changing the order of the switch control signal transmitted to the switch circuit 26 so as to execute the above adjustment.

Figure 9:
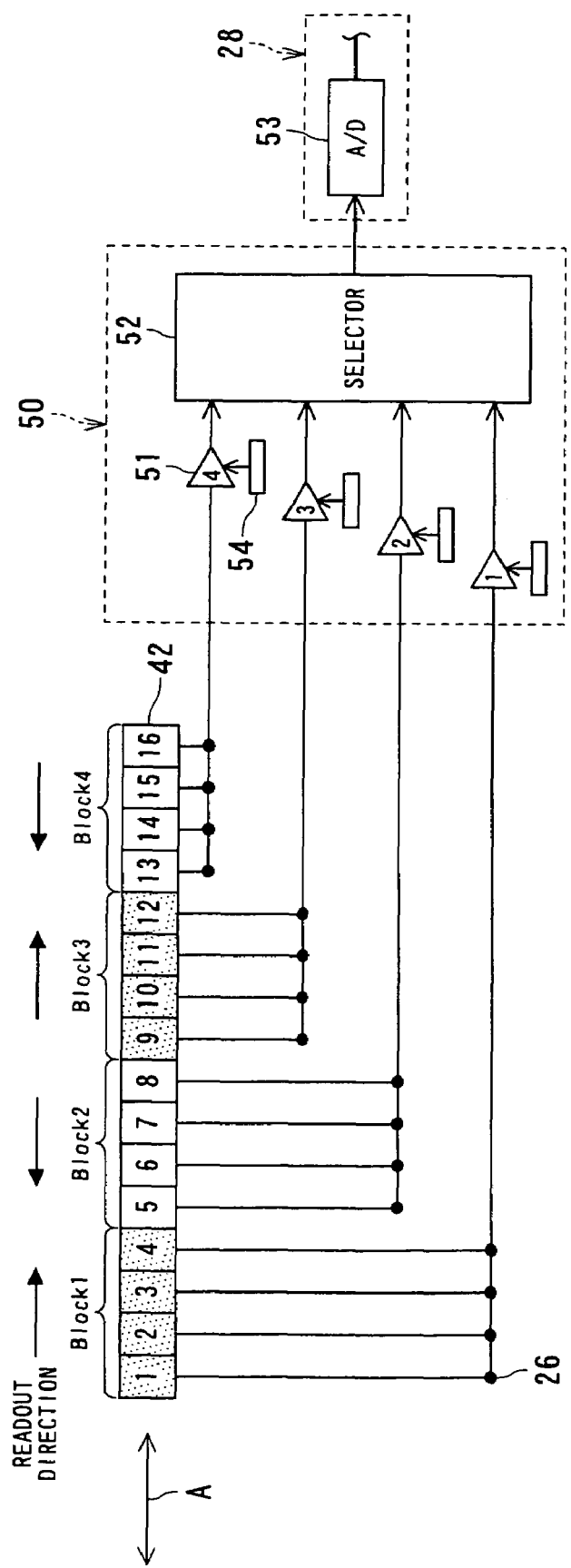
FIG. 9 is a schematic diagram showing an example of changing the readout direction of the electric signals from the detecting elements in the two-dimensional photodiode array detector block shown in FIG. 5.

FIG. 9 is a schematic diagram showing an example of changing the readout direction of the electric signals from the detecting elements 42 in the two-dimensional photodiode array detector block 40 shown in FIG. 5.

Referring to FIG. 9, the readout direction of the electric signals can be controlled by the switch control signal transmitted to the switch circuit 26 from the switch control circuit 27 so as to inverse the readout directions of the electric signals in the adjacent readout blocks. For example, the electric signals are sequentially read-out in the order of row 1, row 2, row 3, and row 4 in block 1, and the electric signals are sequentially read-out in the order of row 8, row 7, row 6, and row 5 in block 2 which is adjacent to the block 1, namely, in the opposite direction of the readout direction of the electric signals in block 1.

Figure 10:
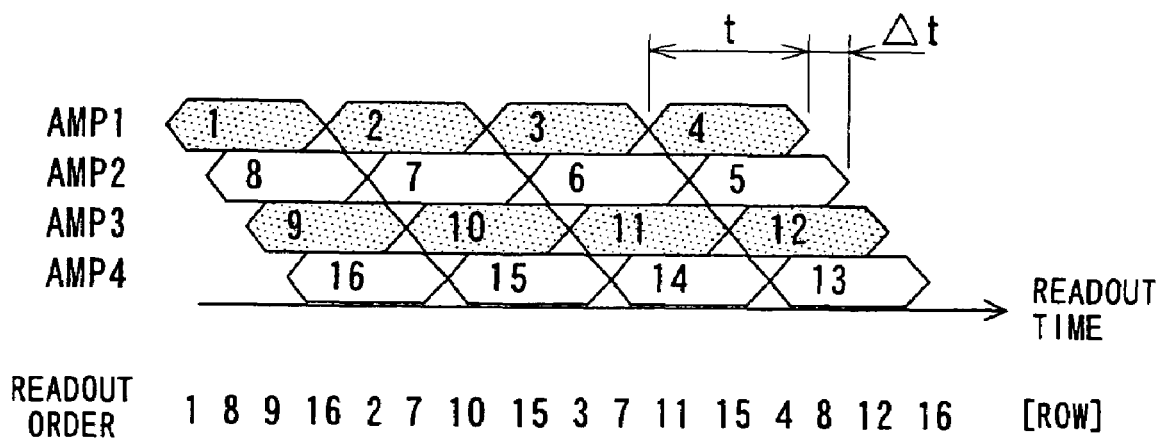
FIG. 10 is a schematic diagram showing the readout time of the electric signals from the detecting elements by the integral amplifiers shown in FIG. 9.

FIG. 10 is a schematic diagram showing the readout time of the electric signals from the detecting elements 42 by the integral amplifiers 51 shown in FIG. 9.

Referring to FIG. 10, the horizontal axis shows the readout time of the electric signals. The relationship between the row as a readout target and the readout time and the order of read-out rows is as shown in FIG. 10 upon reading-out the electric signals from the detecting elements 42 for each row in the readout blocks in the readout direction shown in FIG. 9.

That is, the integral amplifier 51 (AMP 1) sequentially reads-out the electric signals from the block 1 in the order of row 1, row 2, row 3, and row 4. The integral amplifier 51 (AMP 2) sequentially reads-out the electric signals from the block 2 in the order of row 8, row 7, row 6, and row 5. Similarly, the integral amplifiers 51 (AMP 3 and AMP 4) read-out the electric signals from the block 3 in the same direction as that of the block 1 and from the block 4 in the same direction as that of the block 2, respectively.

The readout times of the electric signals in the readout blocks are mutually shifted, thereby setting the operation for reading-out the electric signals in parallel in the order of block 1, block 2, block 3, and block 4. As a result, the readout order of the electric signals in the row direction from the columns in the two-dimensional photodiode array detector block 40 shown in FIG. 9 is row 1, row 8, row 9, row 16, row 2, . . . , row 16, as shown in FIG. 10. Particularly, the readout row next to row 4 that is finally read-out in block 1 is row 5 in block 2, the readout row next to row 8 that is first read-out in block 2 is row 9 in block 3, and the readout row next to row 12 that is finally read-out in block 3 is row 13 in block 4.

That is, in order to reduce the time delay between the readout times upon reading-out the electric signals from the adjacent rows, the readout order or readout direction of the electric signals is controlled by the switch control signal transmitted to the switch circuit 26 from the switch control circuit 27.

Figure 11:
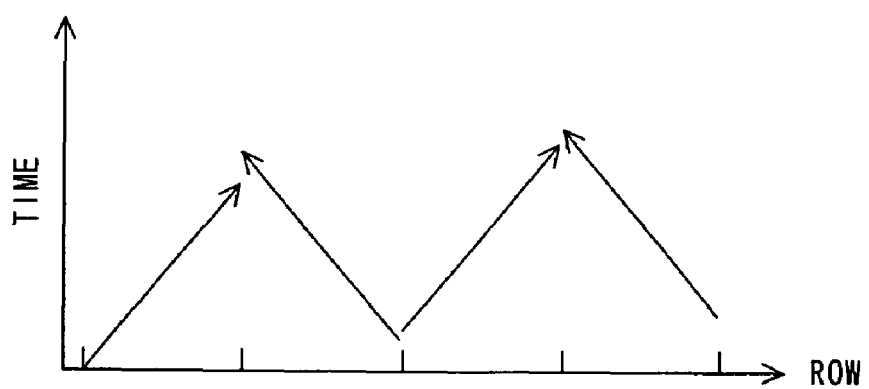
FIG. 11 is a diagram showing the relationship between the row and time upon reading-out the electric signals from the detecting elements in the readout direction shown in FIG. 9.

FIG. 11 is a diagram showing the relationship between the row and time upon reading-out the electric signals from the detecting elements 42 in the readout direction shown in FIG. 9.

Referring to FIG. 11, the vertical axis shows the readout time of the electric signals, and the horizontal axis shows the row of the detecting elements 42 which read-out the electric signals. The detecting elements 42 are divided into the readout blocks in the row direction, and operate in parallel in the readout direction varying depending on the adjacent readout block. As shown in FIG. 11, there is an alternate arrangement of upper-right straight lines for increasing the number of rows in accordance with the time and upper-left straight lines for reducing the number of rows in accordance with the time, and the sum of the number of upper-right straight lines and the number of upper-left straight lines are the number of readout blocks. Since the readout times are shifted for each readout block, the straight lines are shifted in the time direction in accordance with the readout blocks.

The above-read-out electric signals are applied to the data acquisition system 28 and are converted into the digital signals to generate the X-ray detection data. Further, the image reconstructing unit 30 performs the image reconstruction processing of the data, thereby reconstructing the image data. In this case, the electric signals from the detecting elements 42 in the adjacent rows of the radiation detector 23 are read-out with a short time-delay and are used as the X-ray detection data for reconstruction of the image data. Therefore, the deterioration of the image quality of the image data is suppressed.

With the above-mentioned X-ray CT apparatus 20 and radiation detector 23, the demand readout speed of the electric signals read-out from the detecting elements 42 is reduced and thus the circuit design is simplified and the noise of the electric signals is reduced.

That is, the switch circuits 26 are arranged to the detecting elements 42 that are two-dimensionally arranged in the radiation detector 23, the detecting elements 42 are divided into the readout blocks in the row direction, and the switch circuits 26 are operated in parallel between the different readout blocks, thereby reading-out the electric signals in parallel. The switch circuits 26 time-share the electric signals in the same readout block, and sequentially read-out the electric signals. Thus, the number of the signal lines 61 used for readout of the electric signals is reduced and the number of the detecting elements 42 as the readout targets for one of the integral amplifiers 51 is reduced. Thus, the operating speed of the readout circuit 50 for readout of the electric signals is reduced.

As a result, the circuit design of the radiation detector 23 is simplified and the noise of the electric signals is reduced. Further, the speed for readout of the electric signals is reduced and therefore the physical restrictions are relaxed. The two-dimensional photodiode array detector blocks 40 and the detecting elements 42 can be densely arranged and therefore can be connected to the latter-stage data acquisition system 28 via the signal line 61.

In this case, only the control timing of the switch circuit 26 can be adjusted without arranging any specific calculating circuits such as an integrator in the two-dimensional photodiode array detector block 40, thereby performing various processing operations, including the easy analog-adjustment of the readout time and the readout order of the electric signals and the addition process of the electric signals read-out from the detecting elements 42. On the contrary, the circuit space is reduced, the response speed is improved, and the noise performance is improved by arranging a charge/voltage converting circuit such as an integrator near the detecting elements 42.

The time delay is reduced between the readout times of the electric signals from the detecting elements 42 in the adjacent rows by changing the readout directions of the electric signals every readout block, thereby suppressing the image-quality deterioration of the image data.

Figure 12:
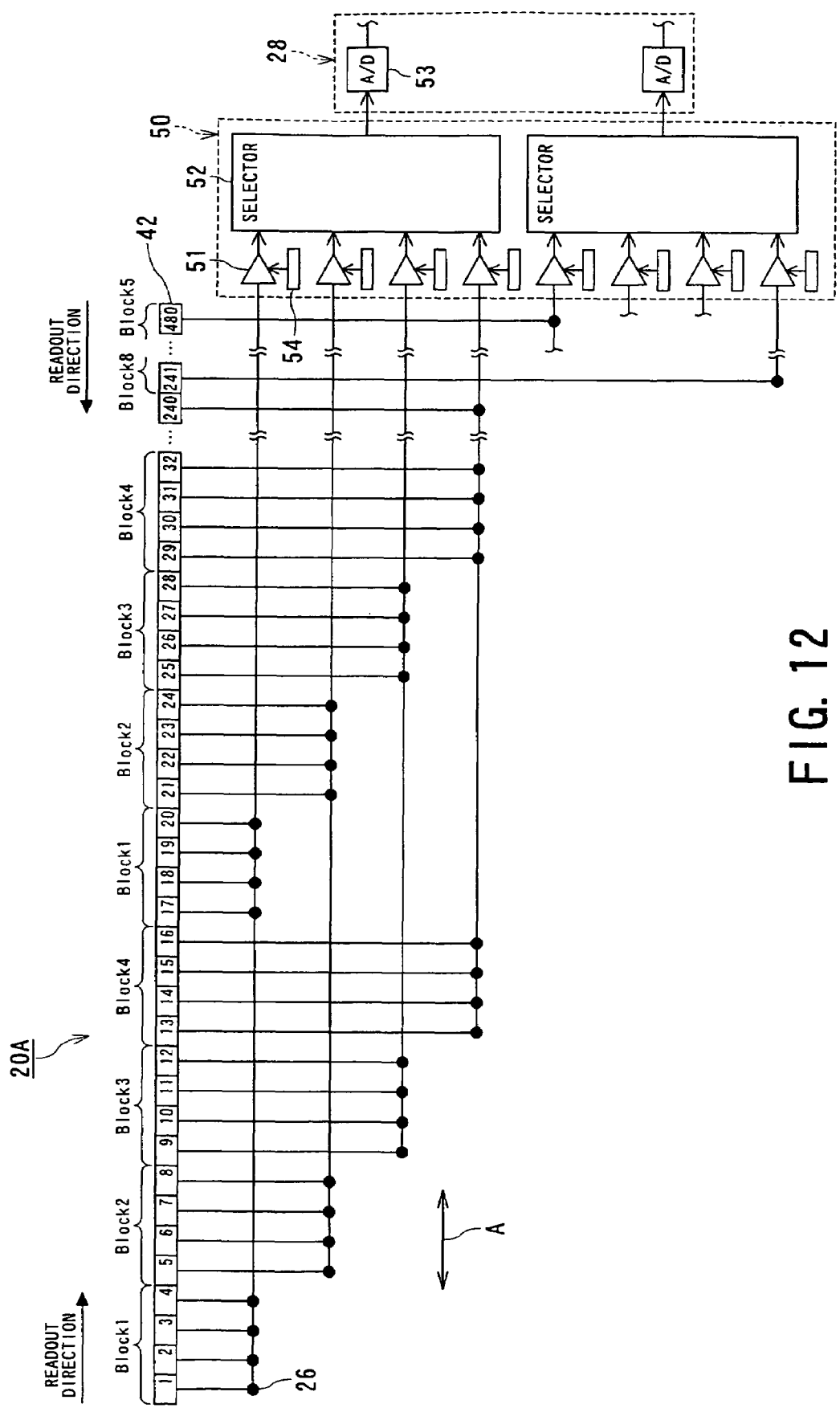
FIG. 12 is a block diagram showing an X-ray CT apparatus according to a second embodiment of the present invention.

FIG. 12 is a block diagram showing an X-ray CT apparatus according to a second embodiment of the present invention.

Referring to FIG. 12, an X-ray CT apparatus 20A is different from the X-ray CT apparatus 20 shown in FIG. 1 in the number of the detecting elements 42, the number of the integral amplifiers 51, and the dividing method to the readout blocks of the detecting elements 42. Other structures and operations are substantially the same as those of the X-ray CT apparatus 20 shown in FIG. 1. Therefore, only the detecting elements 42, the integral amplifiers 51, and related components are shown, the same reference numerals denote the same components, and a description thereof is omitted.

The radiation detector 23 of the X-ray CT apparatus 20A comprises the two-dimensional photodiode array detector blocks 40 having the detecting elements 42 of (480 rows×24 columns) which are two-dimensionally arranged. Referring to FIG. 12, a single column is considered.

The detecting elements 42 are divided into a plurality of, e.g., two, A/D converting blocks in the slice direction A. The detecting elements 42 in the A/D converting blocks are divided into a plurality of, e.g., four, readout blocks (block 1, block 2, block 3, and block 4). The readout block includes not only the group of the adjacent detecting elements 42 in the slice direction A but also the group of the detecting elements 42 which are not adjacent in the slice direction A. As a result, the detecting elements 42 are divided into a total 8 readout blocks.

Referring to FIG. 12, four adjacent detecting-elements 42 are set as one element-group, and adjacent element-groups are sequentially assigned to four different readout-blocks. The element groups, which are at intervals, comprising the four adjacent detecting-elements 42 are included in the common readout block.

The detecting elements 42 in the readout blocks are switchably connected to the common integral amplifiers 51 by the switch circuit 26. Therefore, the number of the integral amplifiers 51 is equal to the number of the readout blocks. Further, the integral amplifiers 51 connected to the detecting elements 42 in one A/D converting block are switchably connected to one common A/D converter 53 via the common selector 52. Similarly, the integral amplifiers 51 connected to the detecting elements 42 in the other A/D converting block are switchably connected to another common A/D converter 53 via the common selector 52.

The integral amplifiers 51 have the amplifier controllers 54 which clear the charges stored in the integral amplifiers 51 at an arbitrary timing.

In the X-ray CT apparatus 20A, the readout direction of the electric signals from the detecting elements 42 in the one A/D converting block to the integral amplifiers 51 is opposite to the readout direction of the electric signals from the detecting elements 42 in the other A/D converting block to the integral amplifiers 51.

Figure 13:
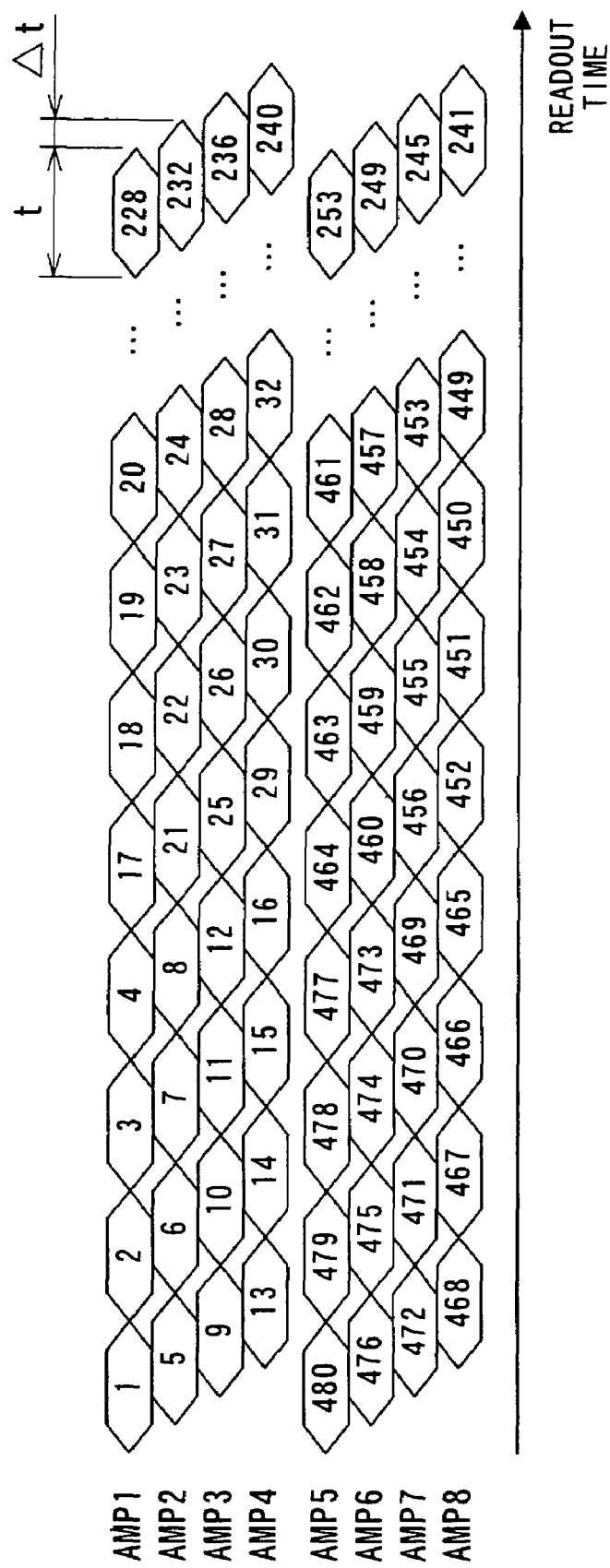
FIG. 13 is a schematic diagram showing the readout time of the electric signals from the detecting elements in the integral amplifiers shown in FIG. 12.

FIG. 13 is a schematic diagram showing the readout time of the electric signals from the detecting elements 42 in the integral amplifiers 51 shown in FIG. 12.

The horizontal axis in FIG. 13 denotes the time. Referring to FIG. 13, the electric signals from the detecting elements 42 in the A/D converting blocks are read-out by the integral amplifiers 51. The electric signals from the common readout block are time-shared and are read-out. However, the electric signals from the different readout blocks are read-out in parallel. The time delay Δt corresponding to the readout time of the A/D converter 53 is set to the electric signals read-out by the integral amplifiers 51 from the detecting elements 42 in the common A/D converting block. On the other hand, the time delay Δt is not set to the electric signals read-out by the integral amplifiers 51 from the detecting elements 42 in the different A/D converting blocks because the electric signals are outputted to the individual A/D converters 53.

Further, the readout directions of the electric signals from the detecting elements 42 in the different A/D converting blocks are opposite to each other so as to reduce the time delay caused in the X-ray detection data obtained by the detecting elements 42 (specifically, the detecting elements 42 in the 241st row and 240th row) adjacently arranged in the different A/D converting blocks.

In the X-ray CT apparatus 20A, a plurality of A/D converters 53 are arranged, the detecting elements 42 are divided into the A/D converting blocks in the slice direction A, and the detecting elements 42 are further divided into a plurality of readout blocks. Therefore, the integral amplifiers 51 can read-out the electric signals from the detecting elements 42 in parallel with each other every A/D converting block and every readout block. Similarly to the X-ray CT apparatus 20 shown in FIG. 1, it is possible to read-out, for a shorter time, the electric signals from the practical two-dimensional photodiode array detector blocks 40 having a large number of rows.

Similarly to the X-ray CT apparatus 20 shown in FIG. 1, in the X-ray CT apparatus 20A, the radiation detector 23 acquires the X-ray detection data in accordance with the slice thickness under the control operation of the timing for clearing the charges stored in the integral amplifiers 51 by the amplifier controller 54.

Figure 14:
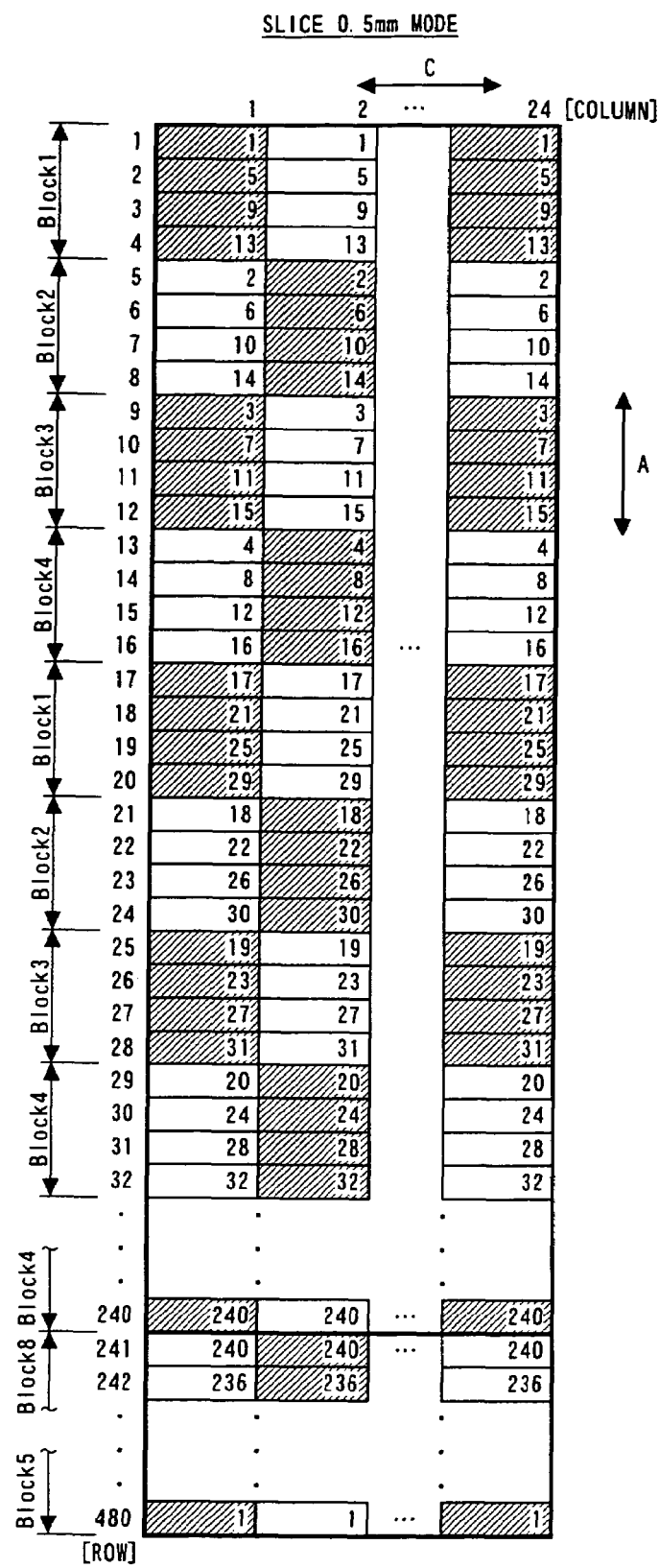
FIG. 14 is a diagram showing the order of the electric signals outputted to the A/D converter from the radiation detector when the X-ray CT apparatus shown in FIG. 13 acquires the X-ray detection data with a slice thickness of 0.5 mm.
Figure 15:
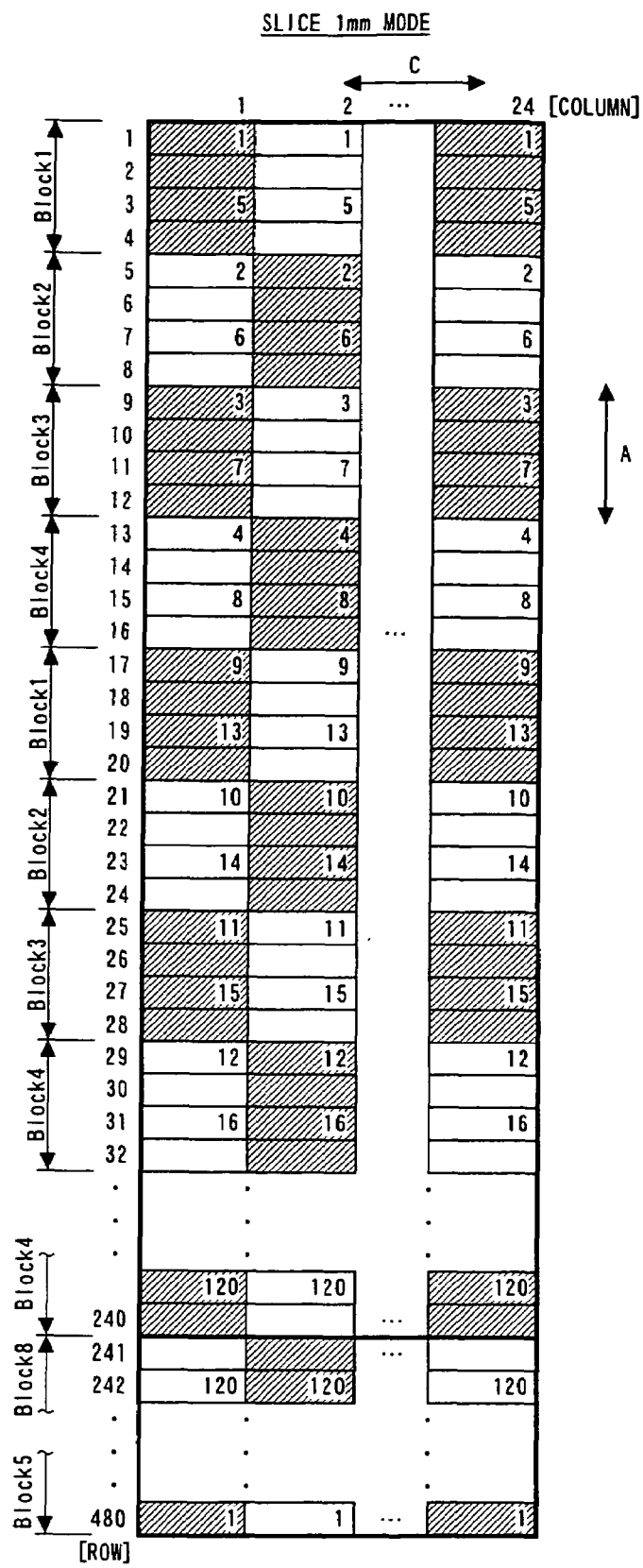
FIG. 15 is a diagram showing the order of the electric signals outputted to the A/D converter from the radiation detector when the X-ray CT apparatus shown in FIG. 13 acquires the X-ray detection data with a slice thickness of 1.0 mm.
Figure 16:
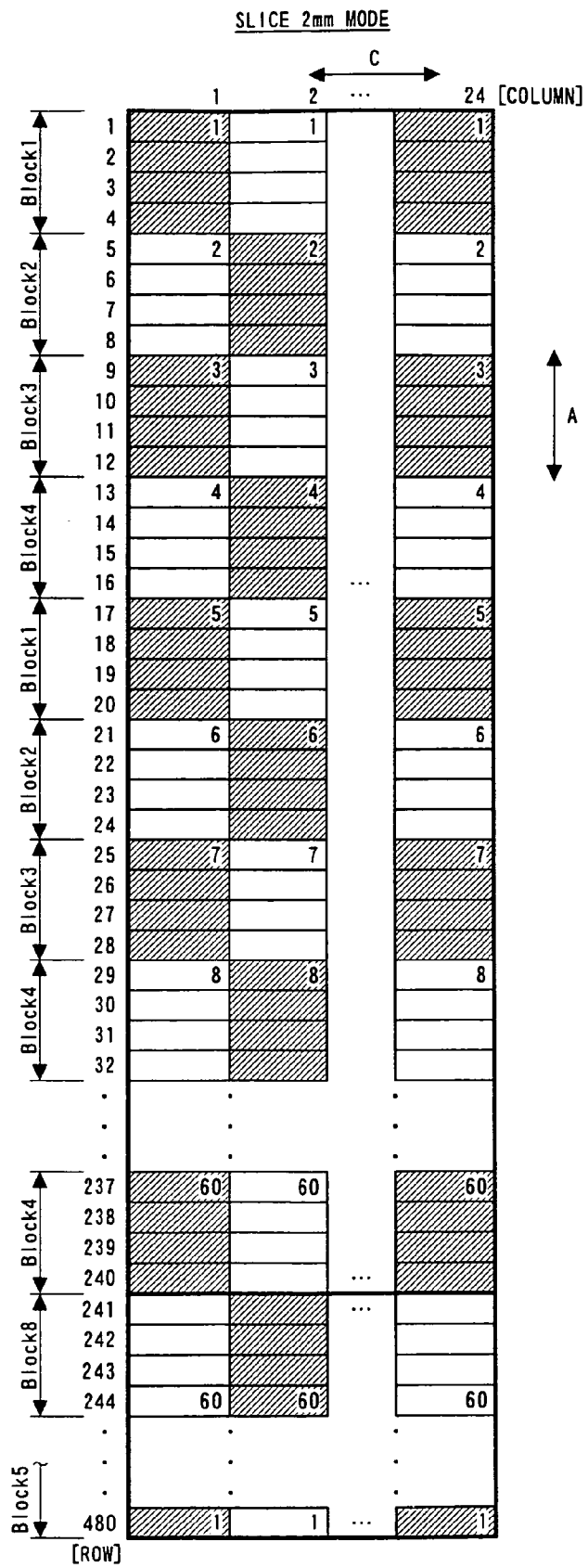
FIG. 16 is a diagram showing the order of the electric signals outputted to the A/D converter from the radiation detector 23 when the X-ray CT apparatus shown in FIG. 13 acquires the X-ray detection data with a slice thickness of 2.0 mm.
Figure 17:
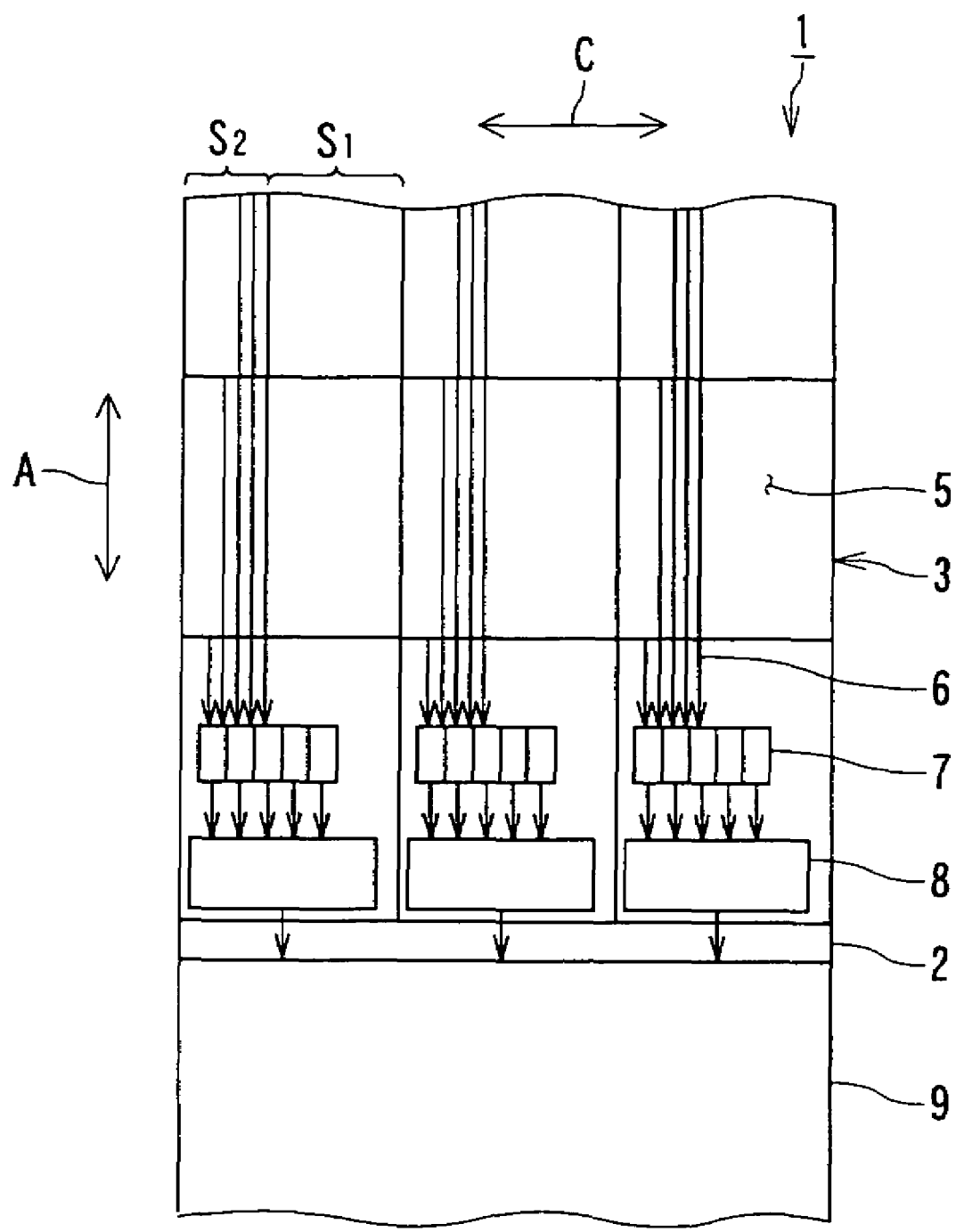
FIG. 17 is a diagram schematically showing one conventional two-dimensional photodiode array detector block.
Figure 18:
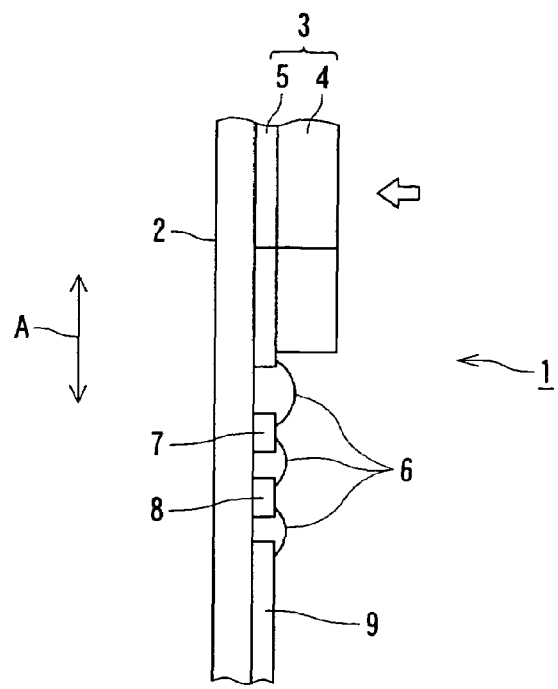
FIG. 18 is a side view showing a conventional two-dimensional photodiode array detector block shown in FIG. 17.
Figure 19:
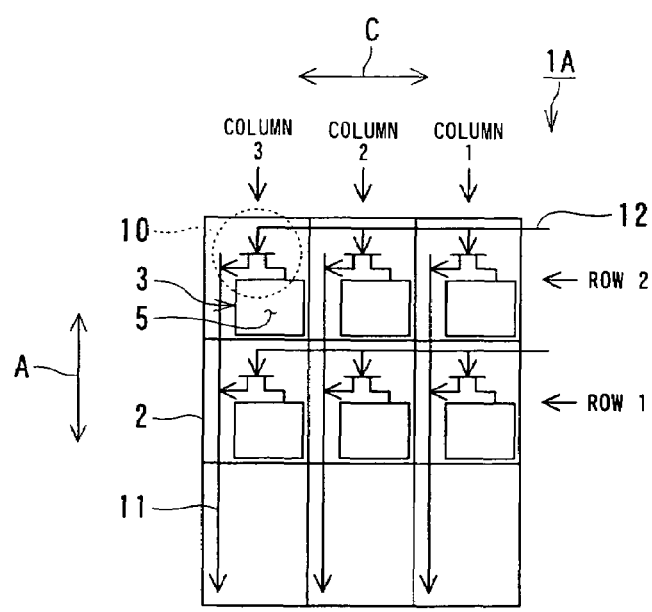
FIG. 19 is a schematic diagram showing another conventional two-dimensional photodiode array detector block which is formed by improving the wiring pattern.
Figure 20:
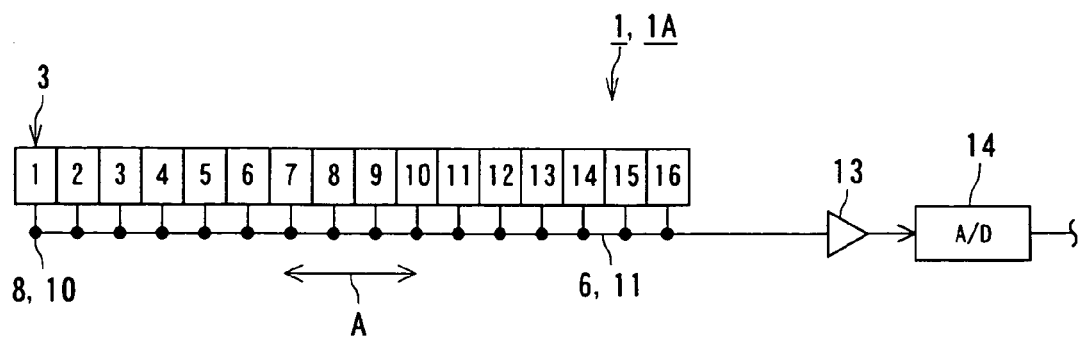
FIG. 20 is a diagram showing a connecting method of the detecting elements and a readout circuit in the conventional two-dimensional photodiode array detector block.
Figure 21:
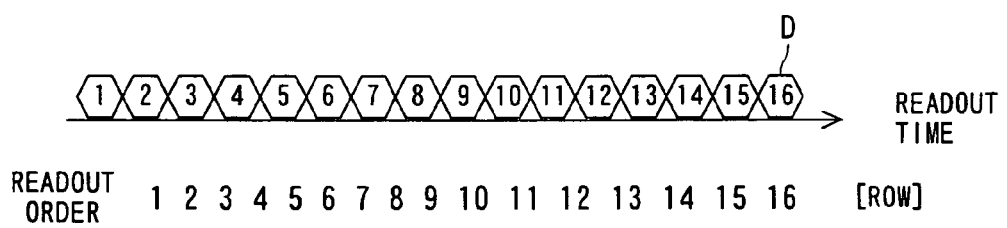
FIG. 21 is a schematic diagram showing a readout time of the electric signal from the conventional detecting elements shown in FIG. 20.

FIG. 14 is a diagram showing the order of the electric signals outputted to the A/D converter 53 from the radiation detector 23 when the X-ray CT apparatus 20A shown in FIG. 13 acquires the X-ray detection data with a slice thickness of 0.5 mm. FIG. 15 is a diagram showing the order of the electric signals outputted to the A/D converter 53 from the radiation detector 23 when the X-ray CT apparatus 20A shown in FIG. 13 acquires the X-ray detection data with a slice thickness of 1.0 mm. FIG. 16 is a diagram showing the order of the electric signals outputted to the A/D converter 53 from the radiation detector 23 when the X-ray CT apparatus 20A shown in FIG. 13 acquires the X-ray detection data with a slice thickness of 2.0 mm.

This slice thickness is set up as a scan condition. According to this slice thickness set up, the control sequences for the switches of respective detecting elements, the integral amplifiers 51, the selectors 52 and so on will be changed.

Referring to FIGS. 14, 15, and 16, a cell denotes the detecting element 42, and the reference numeral in the cell denotes the order of the electric signals outputted to the A/D converter 53. FIGS. 14, 15, and 16 are schematic diagrams showing the two-dimensional arrangement of the detecting elements 42 of (480 rows×24 columns). Now, it is assumed that the single detecting element 42 detects the X-ray detection data with a slice thickness of 0.5 mm.

Referring to FIG. 14, the integral amplifier 51 sequentially outputs the electric signals to the A/D converter 53 at each time for switching the detecting elements 42 for applying the charges to the integral amplifiers 51 by the switch circuit 26, and the amplifier controller 54 clears the charges stored in the integral amplifiers 51. Thus, the A/D converter 53 sequentially reads-out the electric signals equivalent to the integration value of the electric charges accumulated to respective detecting elements. Therefore, the X-ray detection data is acquired with a slice thickness of 0.5 mm by outputting the electric signals to the A/D converter 53 at the timing and the order shown in FIG. 14.

Referring to FIG. 15, each time the detecting element 42 for applying the charges to the integral amplifiers 51 is switched twice by the switch circuit 26, the integral amplifier 51 sequentially outputs the electric signals to the A/D converter 53. Then, the A/D converter 53 sequentially reads-out one electric signal equivalent to the integration value of the electric charges accumulated to two adjacent detecting elements in the slice direction A by clearing the charges stored in the integral amplifier 51 with the amplifier controller 54. Therefore, the X-ray detection data is acquired with a slice thickness of 1 mm by outputting the electric signals to the A/D converter 53 at the timing and the order shown in FIG. 15.

Similarly, referring to FIG. 16, each time the detecting element 42 for applying the charges to the integral amplifiers 51 is switched four times by the switch circuit 26, the integral amplifier 51 sequentially outputs the electric signals to the A/D converter 53. Then, the A/D converter 53 sequentially reads-out one electric signal equivalent to the integration value of the electric charges accumulated to four adjacent detecting elements in the slice direction A by clearing the charges stored in the integral amplifier 51 with the amplifier controller 54. Therefore, the X-ray detection data is acquired with a slice thickness of 2 mm by outputting the electric signals to the A/D converter 53 at the timing and the order shown in FIG. 16.

Upon acquiring the X-ray detection data with slice thickness of 1 mm or 2 mm, the readout orders of the electric signals from the detecting elements 42 to the integral amplifiers 51 are the same as the readout order shown in FIG. 15.

The X-ray detection data can be easily acquired with desired slice thickness by adjusting the timing of the electric signals outputted to the A/D converter.

In the X-ray CT apparatus 20 and the X-ray CT apparatus 20A according to the first and second embodiments, the detecting element 42 may comprise a first storing element and a second storing element which store the charges to reduce the time delay of the electric signals read-out by the integral amplifiers 51 from the adjacent detecting elements 42 in the slice direction A. After the first storing element temporarily stores the charges, the charges are transferred from the first storing element to the second storing element simultaneously or with a short time-delay, and the integral amplifier 51 reads-out the electric signals from the second storing element.

Further, in the X-ray CT apparatus 20A according to the second embodiment, the readout directions of the electric signals by the integral amplifiers 51 are changed to be opposite for each A/D converting block. In addition, the readout directions of the electric signals may be changed to be opposite for each adjacent readout block so that readout times of the electric signals near at least one border of the readout blocks become close each other. The above-mentioned readout directions enable the acquisition of the X-ray detection data with a shorter time-delay in the slice direction.

What is claimed is:

1. An X-ray CT apparatus comprising:
an X-ray generating unit configured to irradiate an X-ray to an object; and
a radiation detector configured to detect the X-ray transmitted through the object;
wherein the radiation detector includes:
a plurality of detecting elements put in two-dimensional positions, and separated into a plurality of readout blocks;
a readout circuit configured to read out electric signals from the detecting elements in the respective readout blocks;
a switch circuit configured to switch the electric signals read out to the readout circuit from the detecting elements at the readout blocks; and
a switch control circuit configured to control the switch circuit so as to read out electric signals with time-sharing from corresponding detecting elements in a common readout block of the readout blocks to the readout circuit and to read out corresponding electric signals in parallel from at least two of the detecting elements to the readout circuit, the at least two of the detecting elements being in different readout blocks from each other,
the radiation detector being configured to make a readout order of the electric signals with time-sharing variable in the respective readout blocks by controlling the switch circuit.

2. An X-ray CT apparatus according to claim 1,
wherein at least one of the readout blocks includes:
a first detecting elements group including some of the detecting elements belonging to adjacent rows; and
a second detecting elements group including others of the detecting elements belonging to other adjacent rows, the second detecting elements group being alienated from the first detecting elements group.

3. An X-ray CT apparatus comprising:
an X-ray generating unit configured to irradiate an X-ray to an object; and
a radiation detector configured to detect the X-ray transmitted the object;
wherein the radiation detector includes:
a plurality of detecting elements put in two-dimensional positions, and separated into a plurality of readout blocks;
a readout circuit configured to read out electric signals from the detecting elements in the respective readout blocks;
a switch circuit configured to switch the electric signals read out to the readout circuit from the detecting elements at the readout blocks, the switch circuit configured to provide transistor switches separately and two-dimensionally to output sides of photodiodes included in the detecting elements; and
a switch control circuit configured to control the switch circuit so as to read out electric signals with time-sharing from corresponding detecting elements in a common readout block of the readout blocks to the readout circuit and to read out corresponding electric signals in parallel from at least two of the detecting elements to the readout circuit, the at least two of the detecting elements being in different readout blocks from each other.

4. An X-ray CT apparatus according to claim 1,
wherein the switch control circuit is configured to change a readout direction of the electric signals with time-sharing in the respective readout blocks so that readout times of at least two of the electric signals with time-sharing become close each other, the two being near at least one border of the readout blocks.

5. An X-ray CT apparatus comprising:
an X-ray generating unit configured to irradiate an X-ray to an object; and
a radiation detector configured to detect the X-ray transmitted the object;
wherein the radiation detector includes:
a plurality of detecting elements put in two-dimensional positions, and separated into a plurality of readout blocks;
a readout circuit configured to read out electric signals from the detecting elements in the respective readout blocks;
a switch circuit configured to switch the electric signals read out to the readout circuit from the detecting elements at the readout blocks; and
a switch control circuit configured to control the switch circuit so as to read out electric signals with time-sharing from corresponding detecting elements in a common readout block of the read out blocks to the readout circuit at a timing according to a slice thickness set up as a scan condition and to read out corresponding electric signals in parallel from at least two of the detecting elements to the readout circuit, the at least two of the detecting elements being in different readout blocks from each other.

6. A method for reading out electric signals of a radiation detector comprising:
separating a plurality of detecting elements put in two-dimensional positions to a plurality of readout blocks; and
reading out electric signals with time-sharing from corresponding detecting elements in a common readout block of the readout blocks, and reading out corresponding electric signals in parallel from at least two of the detecting elements, the two being in the different readout blocks each others,
wherein a readout order of the electric signals with time-sharing is variable in each readout block.

7. A method for reading out electric signals of a radiation detector comprising:
separating a plurality of detecting elements put in two-dimensional positions to a plurality of readout blocks; and
reading out electric signals with time-sharing from corresponding detecting elements in a common readout block of the readout blocks at a timing according to a slice thickness set up as a scan condition, and reading out corresponding electric signals in parallel from at least two of the detecting elements, the two being in the different readout blocks each other.

* * * * *